US012797358B2

(12) United States Patent
Bajrai

(10) Patent No.: US 12,797,358 B2
(45) Date of Patent: Nov. 17, 2026

(54) PLANT-DERIVED SMALL MOLECULES AS MARBURG VIRUS INHIBITORS

(71) Applicant: Leena Hussein Bajrai, Jeddah (SA)

(72) Inventor: Leena Hussein Bajrai, Jeddah (SA)

( * ) Notice: Subject to any disclaimer, the term of this patent is extended or adjusted under 35 U.S.C. 154(b) by 396 days.

(21) Appl. No.: 18/499,733

(22) Filed: Nov. 1, 2023

(65) Prior Publication Data

US 2025/0134850 A1 May 1, 2025

(51) Int. Cl.

| | |
|---|---|
| ***A61K 31/352*** | (2006.01) |
| ***A61K 31/05*** | (2006.01) |
| ***A61K 31/135*** | (2006.01) |
| ***A61K 31/473*** | (2006.01) |
| ***A61K 31/4745*** | (2006.01) |
| ***A61K 31/4965*** | (2006.01) |
| ***A61K 31/53*** | (2006.01) |
| ***A61P 31/14*** | (2006.01) |

(52) U.S. Cl.

CPC ............ *A61K 31/352* (2013.01); *A61K 31/05* (2013.01); *A61K 31/135* (2013.01); *A61K 31/473* (2013.01); *A61K 31/4745* (2013.01); *A61K 31/4965* (2013.01); *A61K 31/53* (2013.01); *A61P 31/14* (2018.01)

(58) Field of Classification Search

None

See application file for complete search history.

(56) References Cited

U.S. PATENT DOCUMENTS

| | | | | |
|---|---|---|---|---|
| 10,293,012 B2 | 5/2019 | Langland et al. | | |
| 10,369,166 B2 | 8/2019 | Vecht-Lifshitz | | |
| 10,987,371 B2 | 4/2021 | Chrétien et al. | | |
| 2016/0151469 A1* | 6/2016 | Ichim ..................... | A61K 39/00 424/85.1 | |

FOREIGN PATENT DOCUMENTS

| | | | | |
|---|---|---|---|---|
| EP | 0093516 A1 * | 11/1983 | .............. | A61P 37/04 |
| WO | WO 99/21005 A2 | 4/1999 | | |

OTHER PUBLICATIONS

Semwal et al. "Health benefits and limitations of rutin—A natural flavonoid with high nutraceutical value," Phytochemistry Letters 46 (2021) 119-128; (Year: 2021).*

Agrawal et al. Rutin: a potential antiviral for repurposing as a SARS-CoV-2 main protease (M pro) inhibitor. Nat Prod Commun 16 (4): 2021. (Year: 2021).*

Zhu et al. "Successful treatment of Marburg virus with orally administrated T-705 (Favipiravir) in a mouse model," Antiviral Research 151 (2018) 39-49. (Year: 2018).*

Bebell et al. "Ebola Virus Disease and Marburg Disease in Pregnancy," Obstetrics & Gynecology 125, 6, 2015. (Year: 2015).*

Onyinye Vivian Mokwelu, "Bioassay Guided Fractionation of Angiotensin Converting Enzyme Inhibitor Compound From *Hypericum perforatum*", UWEScholar—ETD Repository, University of the Western Cape, Aug. 2019, 106 pages.

Rajesh Naithani, et al., "Antiviral Activity of Phytochemicals: A Comprehensive Review", Mini-Reviews in Medicinal Chemistry, vol. 8, Issue 11, 2008, pp. 1106-1133.

Ragupathy Hariprasath et al., "In silico studies of viral protein inhibitors of Marburg virus using phytochemicals from *Andrographis paniculate*", Journal of Applied Biology & Biotechnology, vol. 11, Issue 1, Jan.-Feb. 2023, pp. 222-231.

* cited by examiner

*Primary Examiner* — Jeffrey S Lundgren

*Assistant Examiner* — Michael J Schmitt

(74) *Attorney, Agent, or Firm* — Oblon, McClelland, Maier & Neustadt, L.L.P.

(57) ABSTRACT

The disclosure is directed to a method for preventing or treating viral infections by Marburg virus. The method involves administering kudzuisoflavone A, miquelianin, rutin, and/or protopseudohypericin or their chemical derivatives which interact or inhibit the function of VP35, to a patient who is either currently experiencing a Marburg virus infection or who is at risk on contracting one. Additionally, the disclosure is directed to pharmaceutical compositions, as well as kits, containing kudzuisoflavone A, miquelianin, rutin, and/or protopseudohypericin or their chemical derivatives formulated to perform the method of preventing or treating Marburg virus infection. Methods for evaluating antiviral activity of kudzuisoflavone A, miquelianin, rutin, and/or protopseudohypericin and for screening chemical derivatives of these compounds that exert antiviral activity are also disclosed.

14 Claims, 41 Drawing Sheets

PLANT-DERIVED SMALL MOLECULES AS MARBURG VIRUS INHIBITORS

BACKGROUND OF THE INVENTION

Field of the Invention

The invention pertains to the fields of medical virology and pharmacology, especially to prevention or treatment of Marburg virus disease using compounds found in certain plants that bind to or interact with Marburg virus VP35.

Description of Related Art

Marburg virus is a member of the Filoviridae family which also includes Ebola virus. It causes a severe and often fatal disease known as Marburg virus disease. This disease is typically treated supportively by maintaining hydration, and electrolyte balance and by treating its complications such as bleeding and organ failure. Various treatments of Marburg virus disease have been attempted including administration of antiviral drugs such as remdesivir and favipiravir, active immunization to viral immunogens or antigens, or passive immunization with monoclonal antibodies specific for the virus or with serum from a convalescent patient who has recovered from Marburg virus. Other experimental procedures are under investigation including administration of interfering RNA. However, an effective treatment and prevention of Marburg virus disease remain elusive.

Marburg virus, like the Ebola virus, is a highly virulent member of the family Filoviridae. The Marburg virus was initially discovered in 1967 during outbreaks that occurred in Marburg and Frankfurt, Germany, as well as in Belgrade, Yugoslavia. These outbreaks affected laboratory workers who had been exposed to African green monkeys imported from Uganda. The Marburg virus induces hemorrhagic fever in humans, resulting in a mortality rate of up to 90%. As a result, it is a significant public health concern. The absence of licensed vaccines or specific treatments for Marburg virus infection underscores the urgency for the creation of new therapeutics.

It is one object of the present disclosure to provide methods and compositions for the prevention, reduction of the severity of, and/or treatment of Marburg virus using naturally occurring compounds such as kudzuisoflavone A, miquelianin, rutin, or protopseudohypericin.

BRIEF SUMMARY OF THE INVENTION

One aspect of the disclosure is directed to methods for identifying compounds that interfere with Marburg virus replication and infectivity. The inventors have found that specific types of compounds bind to and interfere with the VP35 protein which is a virulence factor of Marburg virus. These include kudzuisoflavone A, miquelianin, rutin, and protopseudohypericin.

Another aspect of this disclosure is directed to an antiviral or antimicrobial composition or kit comprising kudzuisoflavone A, miquelianin, rutin, and/or protopseudohypericin compounded in a form suitable for administration to a subject exposed to or infected by Marburg virus.

Other aspects of the disclosure are directed to a method for preventing or treating Marburg virus infection by administering kudzuisoflavone A, miquelianin, rutin, and/or protopseudohypericin in an amount that inhibits viral replication, infectivity or virulence, including methods that administer these compounds in amounts that interfere with the function of VP35.

The foregoing paragraphs have been provided by way of general introduction and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings below.

FIG. 2A. Three dimensional protein-ligand interaction energy diagram of the phytochemical compound kudzuisoflavone A.

FIG. 2B. Two dimensional protein-ligand interaction diagram of the phytochemical compound kudzuisoflavone A.

FIG. 2C. Three dimensional protein-ligand interaction diagram of the phytochemical compound miquelianin.

FIG. 2D. Two dimensional protein-ligand interaction diagram of the phytochemical compound miquelianin.

FIG. 2E. Three dimensional protein-ligand interaction diagram of the phytochemical compound rutin.

FIG. 2F. Two dimensional protein-ligand interaction diagram of the phytochemical compound rutin.

FIG. 2G. Three dimensional protein-ligand interaction diagram of the phytochemical compound protopseudohypericin.

FIG. 2H. Two dimensional protein-ligand interaction diagram of the phytochemical compound protopseudohypericin.

FIG. 2I. Three dimensional protein-ligand interaction diagram of the phytochemical compound myricetin.

FIG. 2J. Two dimensional protein-ligand interaction diagram of the phytochemical reference compound myricetin.

DETAILED DESCRIPTION OF THE INVENTION

Figure 1A:
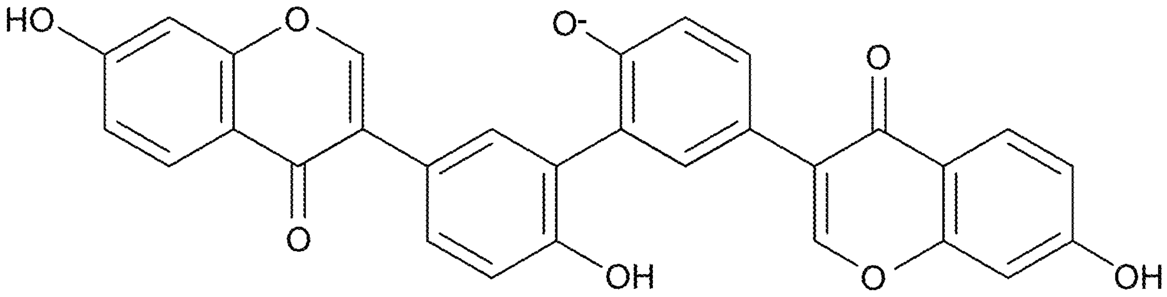
FIGS. 1A-1D depict 2D structures of the top four phytochemicals kudzuisoflavone A (FIG. 1A), miquelianin (FIG. 1), rutin (FIG. 1C), and protopseudohypericin (FIG. 1D) investigated by the inventors.

A thorough in silico drug discovery approach was used to find inhibitors of the RNA binding activity of the Marburg virus VP35 protein. The identification of four inhibitors, namely kudzuisoflavone A, miquelianin, rutin, and protopseudohypericin, was made through virtual screening and post MMGBSA analysis of three medicinal plants, Adiantum *capillus-veneris, Hypericum perforatum*, and *Pueraria montana*, using a library of their phytomolecules. In molecular dynamics (MD) simulations, kudzuisoflavone A and miquelianin showed steady binding to the target protein and favorable interactions with the target protein. Notably, their free binding energies were better than myricetin, a well-known blocker of the VP35 protein of the Ebola virus. The VP35 protein did not exhibit any structural changes with inhibitor interaction, according to principal component analysis (PCA), indicating stable binding. Overall, the inventor's efforts yielded practical and useful information about the molecular interactions and binding dynamics of the identified inhibitors' binding to the VP35 protein of the Marburg virus. Based on these data, the inventor discloses new treatment and prevention methods for Marburg virus disease and methods for identifying compounds interacting with VP35.

The VP35 protein of Marburg virus, which plays a critical role in the virus's replication cycle, was selected as a target. A Marburg virus can elude the host's immune system by decreasing interferon production which is accomplished via the RNA-binding protein VP35. Interferons are host-generated proteins that play a crucial part in the innate immune response by generating an antiviral state in cells. Interferons are created by the host in response to viral infection.

An N-terminal domain that binds RNA and a C-terminal domain that mediates protein-protein interactions make up the two domains that make up the VP35 protein. In order to inhibit the production of interferon by preventing the activation of IRF-3 (interferon regulatory factor-3), the N-terminal domain of VP35 has been demonstrated to bind to double-stranded RNA (dsRNA), which is produced during viral replication.

The inventor proposes treatment or prevention of Marburg virus disease by preventing the VP35 protein's function. Small chemical inhibitors and the creation of VP35-targeting vaccines are two strategies that have been investigated to suppress the activity of VP35. However, there is still a need for the creation of VP35 inhibitors that are more potent and focused, especially those derived from natural sources.

Due to their various chemical makeup and therapeutic qualities, medicinal plants have been a crucial source for the development of new drugs. Numerous bioactive substances found in these plants, such as alkaloids, flavonoids, terpenoids, and phenolic compounds, have been shown to have important pharmacological effects. In order to find new lead molecules for the creation of fresh medications and treatment possibilities, the study of medicinal plants continues to be extremely important.

The Southern maidenhair fern, or Adiantum *capillus-veneris*, has a number of therapeutic qualities, including antiviral actions. Studies have shown that extracts from Adiantum capillus-veneris have strong antiviral effects against the human immunodeficiency virus (HIV) and herpes simplex virus type 1 (HSV-1). St. John's wort, also known as *Hypericum* perforatum, is renowned for its traditional therapeutic applications. Antiviral qualities of this plant have been discovered to be effective against a variety of viruses, including HIV, herpes simplex virus, and influenza A. And finally, kudzu, or *Pueraria montana*, is valued for its therapeutic properties. It has bioactive substances that are antiviral and effective against influenza viruses, particularly H1N1. According to several studies the three herbs Adiantum *capillus-veneris, Hypericum perforatum*, and *Pueraria montana* have promising antiviral potential.

Computational techniques have become an effective tool in recent years for the discovery of prospective medication candidates from medicinal plants. In particular, virtual screening has gained popularity as a tool for finding new drugs. This method involves using computer simulations to estimate the binding affinity of small compounds to a target protein. Virtual screening can significantly reduce the time and cost of drug discovery by enabling researchers to identify potential drug candidates in silico before conducting expensive and time-consuming experimental assays.

An in silico drug discovery protocol was used to identify potential phytomolecules from three medicinal plants viz; Adiantum *capillus-veneris, Hypericum perforatum*, and *Pueraria montana* that can inhibit the VP35 protein's RNA binding activity, e.g., to provide a list of potential natural inhibitors from Adiantum *capillus-veneris, Hypericum perforatum*, and *Pueraria montana* that can be used as a starting point for further experimental validation.

The term "subject" encompasses subjects susceptible to infection or carrier status by a filoviridae or Marburg virus. This includes humans and other mammals like fruit bats as well as viral vectors for filovirus or Marburg virus strains. Certain occupations, such as veterinarians, laboratory or quarantine facility workers who handle non-human primates from Africa, or miners, may also be at increased risk of exposure to Marburg viruses. This term includes male and females as well as young and old subjects. For example, it includes adult human males and females greater than 0, 1, 2, 5, 10, 20, 30, 40, 50, 60, 70, 80, 90, or 100 years of age as well as adult and non-adult mammals. It includes subjects of different races or geographic or national origin. It includes subjects from countries which have had out breaks of Marburg virus or countries suspected of having endemic Marburg virus, including Angola, DR Congo, Equatorial Guinea, Germany, Ghana, Guinea, Kenya, Serbia, South Africa, Tanzania and Uganda. It includes healthy subjects as well as those having infectious, metabolic, respiratory, or cardiovascular diseases.

The term Filoviridae is used herein to describe five genera in the filovirus family: Ebolavirus, Marburgvirus, Cuevavirus, Striavirus, and Thamnovirus. The methods and compositions disclosed herein may be used to prevent or inhibit infection by filoviruses including filoviruses expressing a VP35 protein or an isotype thereof. Preferably, the filovirus is Marburg virus and the preferred subject is a human or a filovirus vector such as a fruit bat. Members of the filoviridae family are described by and incorporated by reference to ARCH VIROL. 2010 December; 155(12): 2083-2103.

Marburg virus encompasses the species Marburg marburgvirus includes other members of the genus Marburgvirus. All six Marburg virus strains (Musoke, Ratayczak, Popp, Voege, Ozolin, and Marburg Ravn) are considered to be pathogenic. No serological cross-reactivity is observed with Ebola virus, the other important pathogenic filovirus. The methods and compositions disclosed herein may be deployed for prevention or treatment of Marburg virus diseases by any of the strains disclosed above.

As disclosed herein molecular docking (MD) simulations were used to evaluated binding affinities. The top for phytomolecules, Kudzuisoflavone A, Miquelianin, Rutin, and Protopseudohypericin were selected for their binding interactions with the protein. Results showed promising interactions and predicted high affinity binding. The 2D structures of these four compounds are described in FIGS. 1A-1D.

Kudzuisoflavone A is a compound found in kudzu, a plant that has been used in traditional Chinese medicine. Kudzu roots are rich in isoflavones, including kudzuisoflavone A, puerarin, daidzein, and daidzin. Isoflavones are a type of phytoestrogen, which are plant compounds that have estrogen-like effects in the body. In preferred embodiments of the compositions and methods disclosed herein an isolated or purified form of this compound is used. In other embodiments this compound may be administered in combination with other isoflavones or kudzu extracts including the plant compounds mentioned above. FIG. 1A describes its 2D chemical structure. In some embodiments derivatives of Kudzuisoflavone A, may be employed in the invention. These include derivatives with other hydroxyl, methoxy, methyl, $C_2$-$C_6$ alkyl, phenyl or other aryl, and acylated, acetylated, sulfated, or esterified forms. In some instances, a hydroxy group may be substituted with a glycoside, such as with glucose, galactose, rhamnose, or glucuronic acid to improve or modulate solubility or affect other pharmacokinetic of pharmacodynamic properties.

Figure 1B:
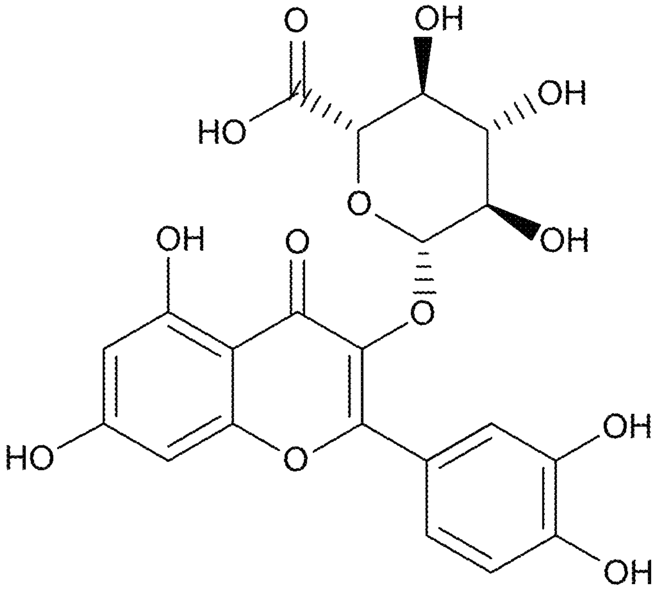

Miquelianin (quercetin 3-O-glucuronide) is a flavonol glucuronide, a type of phenolic compound present in wine, in species of St John's wort, like *Hypericum hirsutum*, in *Nelumbo nucifera* (Indian lotus) or in green beans. Preferably it is administered in a purified or isolated form such as one that is commercially available, but in some embodiments may be administered in combination with other materials it is naturally associated with. Further description and sourcing of this compound is incorporated by reference to the following documents: Ghiselli, A.; Nardini, M., Baldi, A.; Scaccini, C. (1998). "Antioxidant Activity of Different Phenolic Fractions Separated from an Italian Red Wine". *Journal of Agricultural and Food Chemistry.* 46 (2): 361-367. doi:10.1021/jf970486b. PMID 10554247; Wei, Y.; Xie, Q.; Dong W., Ito, Y. (2009). "Separation of epigallocatechin and flavonoids from *Hypericum* perforatum L. By high-speed counter-current chromatography and preparative high-performance liquid chromatography". *Journal of Chromatography* A, 1216 (19): 4313-4318. doi:10.1016/j chroma.2008.12.056. PMC 277,7726. PM ID 19150073; Kitanov, GI. MI. (1988). "Miquelianin and other polyphenols from *Hypericum hirsutum". Chemistry of Natural Compounds.* 24: 119-120. doi:10.1007/BF00597593. S2CID 37846890. Kashiwada, Y.; Aoshima, A.; Ikeshiro, Y.; Chen, Y. P.; Furukawa, H.; Itoigawva, M.; Fujioka, T.; Mihashi, K.; Cosentino, L. M.; Morris-Natschke, S. L.; Lee, K. H. (2005). "Anti-f-IV benzylisoquinoline alkaloids and flavonoids from the leaves of *Nelumbo nucifera*, and structure--activity correlations with related alkaloids". *Bioorganic & Medicinal Chemistry.* 13 (2): 443-448. doi:10.1016/j.bmc.2004.10.020. PMID 15598565. Plumb, G. W.; Price, K. R.; Williamson, G. (1999). "Antioxidant properties of flavonol glycosides from green beans". *Redox Report.* 4 (3): 123-127. doi:10.1179/135100099101534800. PMID 10496415. FIG. 1B describes its 2D chemical structure. In some embodiments derivatives of Miquelianin may be employed in the invention. These include derivatives with other hydroxyl, methoxy, methyl, $C_2$-$C_6$ alkyl, phenyl or other aryl, and acylated, acetylated, sulfated, or esterified forms. In some instances, a hydroxy group may be substituted with a glycoside, such as with glucose, galactose, rhamnose, or glucuronic acid to improve or modulate solubility or affect other pharmacokinetic of pharmacodynamic properties.

Figure 1C:
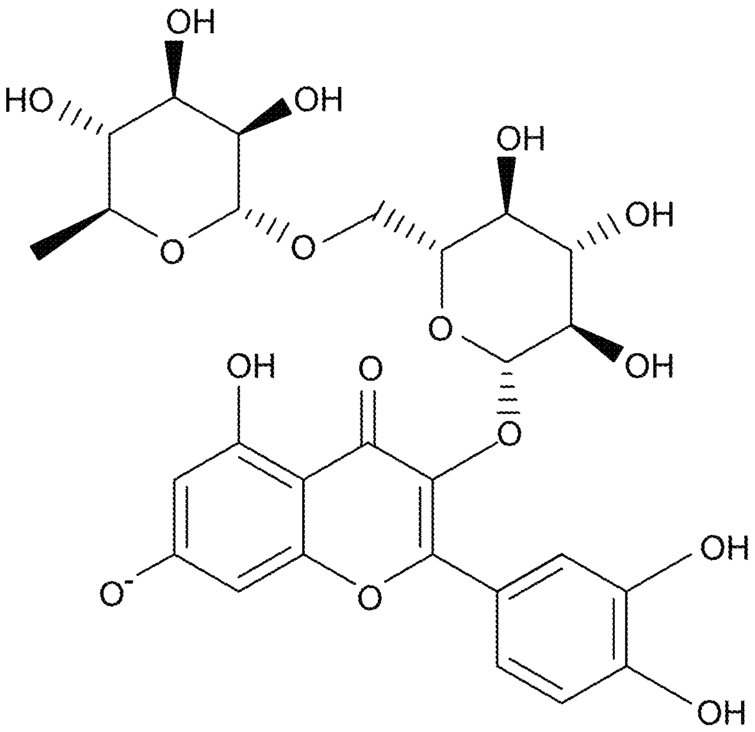

Rutin (rutoside, quercetin-3-O-rutinoside, or sophorin) is a glycoside combining the flavonol quercetin and the disaccharide rutinose (α-L-rhamnopyranosyl-(1→6)-β-D-glucopyranose). It is a flavonoid glycoside found in a wide variety of plants, including citrus. Preferably an isolated or purified rutin is incorporated in the compositions and methods of the invention. Additional information about rutin including sources, biosynthesis and methods for preparation, and bioavailability is described by, and incorporated by reference to <https://en.wikipedia.org/wiki/Rutin>(last accessed Aug. 24, 2023) and to Merck Index, 12th Edition, 8456 and Krewson C F, Naghski J (November 1952). "Some physical properties of rutin". *Journal of the American Pharmaceutical Association.* 41 (11): 582-587. doi:10.1002/jps.3030411106. PMID 12999623. FIG. 1C describes its 2D chemical structure. In some embodiments derivatives of Rutin may be employed in the invention. These include derivatives with other hydroxyl, methoxy, methyl, $C_2$-$C_6$ alkyl, phenyl or other aryl, and acylated, acetylated, sulfated, or esterified forms. In some instances, a hydroxy group may be substituted with a glycoside, such as with glucose, galactose, rhamnose, or glucuronic acid to improve or modulate solubility or affect other pharmacokinetic of pharmacodynamic properties.

Figure 1D:
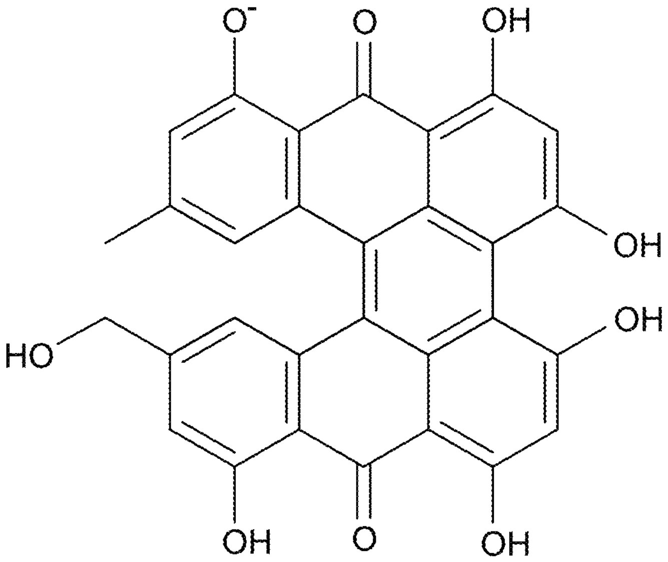
Figure 1E:
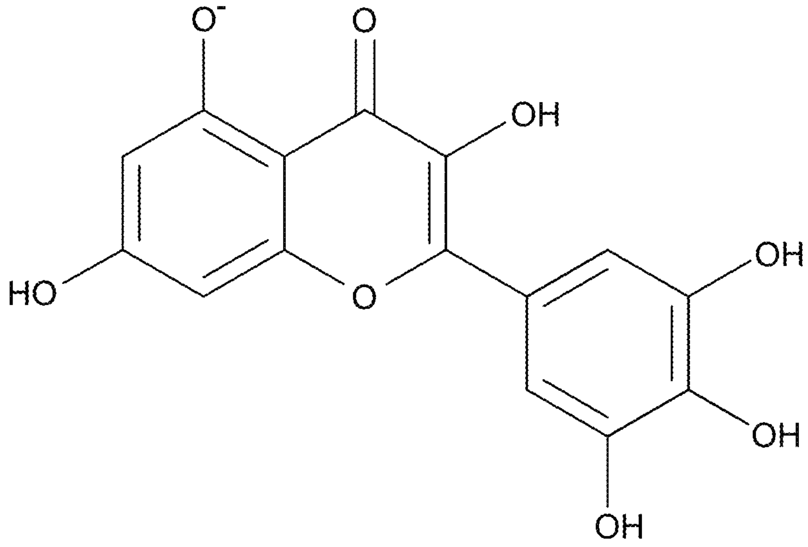
FIG. 1E depicts the 2D structure of myricetin, a reference compound.

Protopseudohypericin is a naturally occurring compound that can be isolated from H. perforatum (St. John's Wort) or H. annulatum. Preferably it is administered in a purified or isolated form such as one that is commercially available, but in some embodiments may be administered in combination with other materials it is naturally associated with. Further information about this compound is described by and incorporated by reference to National Center for Biotechnology Information (2023). PubChem Compound Summary for CID 171335, Protopseudohypericin. Retrieved Aug. 24, 2023 from <https://pubchem.ncbi.nlm.nih.gov/compound/Protopseudohypericin>. FIG. 1D describes its 2D chemical structure. In some embodiments derivatives of Protopseudohypericin may be employed in the invention. These include derivatives with other hydroxyl, methoxy, methyl, C2-C6 alkyl, phenyl or other aryl, and acylated, acetylated, sulfated, or esterified forms. In some instances, a hydroxy group may be substituted with a glycoside, such as with glucose, galactose, rhamnose, or glucuronic acid to improve or modulate solubility or affect other pharmacokinetic of pharmacodynamic properties.

Electrolytes is a term used herein to describes compounds and/or minerals typically includes those lost during infection with Marburg virus including sodium, potassium, calcium, bicarbonate, magnesium and chloride. Typically these are in hydrated form such as an oral rehydration solution, such as WHO ORS, or an intravenous drip. In some embodiments glucose is included.

In some embodiments, a patient infected with or at risk of infection with Marburg virus or other filovirus may be administered zinc, manganese, iron, selenium or copper or be administered vitamins including vitamin A, B vitamins such as B6 or B123, vitamin C, vitamin D or vitamin E. Such minerals or vitamins may be administered in combination with or in addition to kudzuisoflavone A, miquelianin, rutin, and protopseudohypericin.

The compositions disclosed herein typically comprise at least one of kudzuisoflavone A, miquelianin, rutin, and protopseudohypericin preferably in an amount that inhibits replication of Marburg viruses and in an amount that inhibits an activity of VP35 or that antagonizes this viral protein. When used for pharmaceutical purposes, the kudzuisoflavone A, miquelianin, rutin, and protopseudohypericin may be generally formulated with a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described Good, N.E., et cl. (1966) *Nydrcgen Ion Bufiers for Biological Research.* BCHEMISTRY. 5(2): 467-77—incorporated herein by reference in its entirety.

The compositions can additionally include a stabilizer, enhancer or other pharmaceutically acceptable carriers or vehicles. A pharmaceutically acceptable carrier can contain a physiologically acceptable compound that acts, for example, to stabilize the compounds. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. Examples of carriers, stabilizers or adjuvants can be found in Remington's Pharmaceutical Sciences, $21^{st}$ edition, supra.

In some embodiments, the composition comprising kudzuisoflavone A, miquelianin, rutin, and/or protopseudohypericin will comprise a carrier or excipient not found in nature such as liposomes, polymeric nanoparticles, dendrimers, micelles, carbon nanotubes, inorganic nanoparticles, polymeric microspheres, or hydrogels. In such compositions the kudzuisoflavone A, miquelianin, rutin, and/or protopseudohypericin may be free in solution or covalently or non-covalently linked, coated, or embedded in the carrier.

Kudzuisoflavone A, miquelianin, rutin, and/or protopseudohypericin or their derivatives may be administered via a liposome. For example, they may be encapsulated in a liposome or encapsulated within a liposome which has its surface modified with a ligand, antibody, or antibody fragment that binds to viral antigens or host antigens that are upregulated during viral infection. A liposome encapsulating kudzuisoflavone A, miquelianin, rutin, and/or protopseudohypericin or their derivatives may be formulated to release its encapsulate contents inside of an endosome such as a pH sensitive liposome that releases its contents inside of an acidic endosome. Liposomes are typically produced from a phospholipid such as phosphatidylcholine or phosphatidylserine and aqueous phase. Liposomes may be produced by a thin-film hydration method or by reversed phase evaporation or by sonication.

A person skilled in the art will appreciate that kudzuisoflavone A, miquelianin, rutin, or protopseudohypericin (or other added active ingredients) can be appropriately formulated into a pharmaceutical composition for administration to a subject.

The amount of pharmaceutically acceptable carrier will depend upon the level of the compound and any other optional ingredients that a person skilled in the art would classify as distinct from the carrier such as other active agents.

When other active agents are present in the pharmaceutical formulation of the present invention, the dose of the compound may either be the same as or differ from that employed when the other additional components are not present. Appropriate doses will be readily appreciated by those skilled in the art.

Powders and tablets may contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Liquid pharmaceutical compositions include, for example, solutions suitable for oral or parenteral administration, suspensions, and emulsions suitable for oral administration. Sterile water solutions of the active component (e.g., kudzuisoflavone A, miquelianin, rutin, and protopseudohypericin) or sterile solutions of the active component in solvents comprising water, buffered water, saline, PBS, ethanol, propylene glycol, pharmaceutically acceptable oily or hydrophobic ingredients which may be in the form of an emulsion, are examples of liquid compositions suitable for parenteral administration.

The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., kudzuisoflavone A, miquelianin, rutin, and protopseudohypericin) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, for example from 5, 6, 7, 8 to 9, or from 7 to 8.

Single or multiple administrations of the pharmaceutical compositions can be carried out with dose levels and pattern being selected by the treating practitioner. In any event, the pharmaceutical formulations should provide a quantity of kudzuisoflavone A, miquelianin, rutin, or protopseudohypericin sufficient to effectively treat or prevent a Marburg virus or other filovirus infection in the patient.

In some embodiments kudzuisoflavone A, miquelianin, rutin, or protopseudohypericin is administered to the subject as a single therapy for the treatment or prevention of a viral infection. Such a single therapy may be accompanied by a carrier or excipient that enhances the pharmacokinetic or pharmacodynamic properties of the active ingredient, such as promoting its uptake or release into the blood stream or other biological components which may be virus infected or prolonging its biological half-life.

In other embodiments, a combination therapy comprising administering two or more of kudzuisoflavone A, miquelianin, rutin, or protopseudohypericin or additional antiviral drugs, agents or therapies is used to treat a subject.

The effective dosage of the formulations will vary depending on many different factors, including means of administration, target site, physiological state of the patient, and other medicines administered. Thus, treatment dosages will need to be titrated to optimize safety and efficacy. In determining the effective amount of a compound to be administered, the physician should evaluate the particular compound being used, the filovirus disease state being diagnosed; the age, weight, and overall condition of the patient, progression of the disease, and use of other drug regimens. The size of the dose also will be determined by the existence, nature, and extent of any adverse side-effects that accompany the administration of the active compound. In some embodiments, doses may range between about 0.01, 0.02, 0.05, 0.1, 0.2, 0.5, 1.0, 2.0, 5.0, 10.0, 20.0, 50.0 to and 100 μg per kilogram of body weight, for example from between about 0.1 and about 50 g per kg of body weight. The ranges above include all intermediate subranges and values.

In some embodiments, the pharmaceutical composition comprises a therapeutically effective amount of kudzuisoflavone A, miquelianin, rutin, or protopseudohypericin. The content of the of kudzuisoflavone A, miquelianin, rutin, or protopseudohypericin in the pharmaceutical composition is, for example, from about 0.1%. 0.2%, 0.5%, 1.0%, 2.0%, 5.0%, 10.0%, 2.0%, 50.0% to about 100% w/w of the pharmaceutical composition. This range includes all intermediate subranges and values. In one example, the pharmaceutical composition comprises a therapeutically effective amount of an active compound that improves the subject's condition or prognosis. In one example, the pharmaceutical composition comprises a therapeutically effective amount of an active compound disclosed herein to reduce replication or transmission of filovirus such as Marburg virus. In one example, the pharmaceutical composition comprises a therapeutically effective amount of a compound disclosed herein to inhibit a VP35 activity.

The disclosure provides pharmaceutical formulations or compositions, both for veterinary and for human medical use, which comprise one or more of kudzuisoflavone A, miquelianin, rutin, or protopseudohypericin, which may or may not be in combination with each other or with one or more other antiviral compounds. The active agents may be further compounded or admixed with one or more pharmaceutically acceptable carriers and/or excipients and optionally any other therapeutic ingredients, stabilizers, or the like.

Carriers is a term used herein to describe material that are pharmaceutically acceptable in the sense of being compatible with the other ingredients, such as sugars, hydroxyethylstarch (HES), dextrates (e.g., cyclodextrins, such as 2-hydroxypropyl-β-cyclodextrin and sulfobutylether-β-cyclodextrin), polyethylene glycols, and pectin. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions are listed in "*Remington: The Science & Practice of Pharmacy*" 21st edition, supra; or in "Handbook of Pharmaceutical Excipients", Third Ed., Ed. A. H. Kibbe, Pharmaceutical Press, 2000—incorporated herein by reference in its entirety.

Modes of administration include all those described by, and incorporated by reference to Kim 0.1, De Jesus 0. *Medication Routes of Administration*. [Updated 2023 Feb 12]. In: StatPearis [Internet]. Treasure Island (FL): StatPearls Publishing; 2023—incorporated herein by reference in its entirety. These include without limitation enteral administration such as oral, sublingual, buccal or rectal routes; parenteral administration including intravenous injection, intralymphatic injection, intrasplenic administration, administration to the skin or mucous membranes, administration to the bone marrow, administration to the thymus, administration to Peyer's patches or tonsils, intramuscular administration, subcutaneous injection, intraarterial administration; other modes of administration include trans nasal administration, administration by inhalation, vaginal administration, transdermal administration, intraorgan administration, administration to the brain and nervous system, and intraosseous administration. Typically a route of administration will be determined by a medical professional that delivers the active compound to a bodily site infected with or at risk of infection by filovirus, such as by Marburg virus. In one embodiment, immune cells including buffy coat cells, white blood cells, lymphocytes, and macrophages may be treated ex vivo or in vitro with kudzuisoflavone A, miquelianin, rutin, or protopseudohypericin or their chemical derivatives that bind to or otherwise interfere with VP35 function.

The pharmaceutical compositions disclosed herein may be suitable for use in a variety of drug delivery systems. Suitable formulations for use in the present disclosure may be found in Remington's Pharmaceutical Sciences, 21st edition *Remington, the science and practice of pharmacy*. (1995). Easton, Pa. Mack Pub. Co., which is incorporated by reference especially for formulation of compositions comprising at least one of kudzuisoflavone A, miquelianin, rutin, and protopseudohypericin for oral, parenteral, topical and other modes of administration. In some cases, a drug delivery system such as those using a pump or catheter may be employed to deliver the active compound or composition Modes of drug delivery suitable for formulation of the four compounds disclosed herein are described by and incorporated by reference to Langer R. *New methods of drug delivery*. Science. 1990 Sep. 28; 249(4976):1527-33. doi: 10.1126/science.2218494. PMID: 2218494.

Embodiments of the invention include but are not limited to the following.

A method for treating a subject exposed to or infected by Marburg virus comprising administering to the subject at least one of kudzuisoflavone A, miquelianin, rutin, or protopseudohypericin or chemical derivatives thereof that bind to or interact with VP35 in an amount sufficient to bind to, antagonize, or inhibit activity of Marburg virus VP35 protein. This method may be performed on a subject who has been exposed to Marburg virus., is at risk of exposure to Marburg virus, or who has been infected by Marburg virus.

Figure 1F:
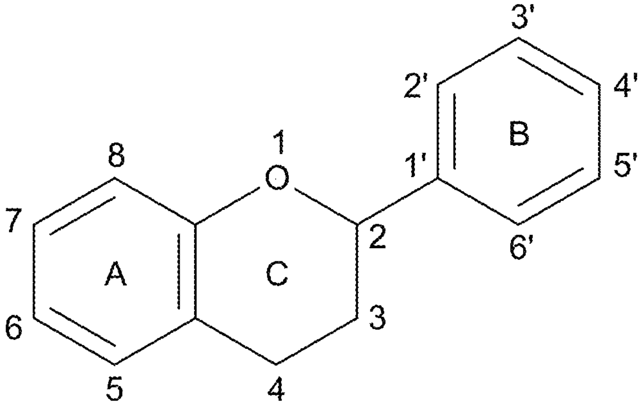
FIGS. 1F-1H show the 2D structures of a glycone (FIG. 1F), a flavonol (FIG. 1G), and Q3G (FIG. 1H). Quercetin-3-3-O-D-glucoside (Q3G) is a flavonoid and also called isoquercetin, quercetin-3-glucoside, quercetin-3-O-glucoside, Quercetin-3-D-glucoside. The analogues of Q3G includes other quercetin glycosides such as enzymatically modified isoquercitrin (EMIQ), a polyglycosylated Q3G analogue, rutinoside, or rutoside (also called rutine or sophorine). In addition, miquelianin (quercetin 3-O-β-d glucuropyranoside) and rutin (quercetin 3-O-β-d-(6"-α-1-rhamnosylo)-glucopyranoside) are flavonoids too and differ from other quercetin derivatives in flavonols group (yellow color) of the basic flavonoid structure (glycone). Other compounds having the glycone structure of FIG. 1F, the flavonol structure of FIG. 1G or a Q3G structure of FIG. 1H may exhibit antiviral activity such as binding to or interference of VP35 activity.
Figure 1G:
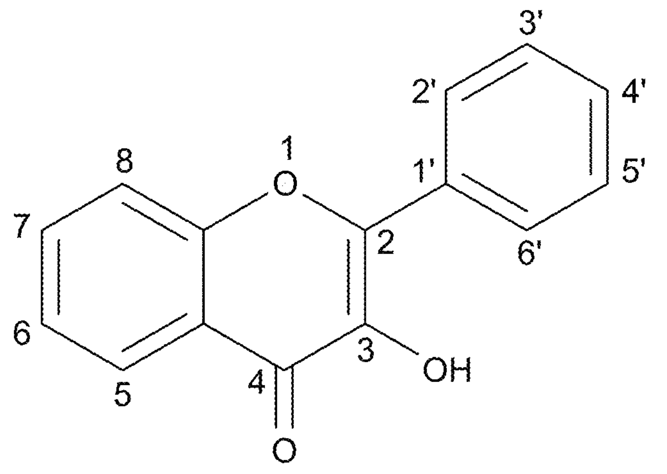
Figure 1H:
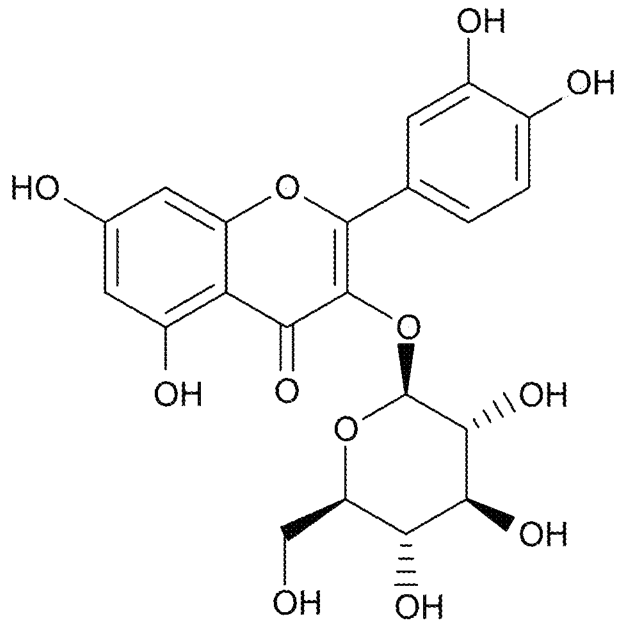

Chemical derivatives of kudzuisoflavone A, miquelianin, rutin, or protopseudohypericin include compound with a glycone or flavonol core structure such as those in FIGS. 1F, 1G and 1J with one or more hydroxy or carboxy substituents on these core structures or one or more of the corresponding hydroxy or carboxy substituents on the structures shown by FIGS. 1A-1E. Also, included are Q3G or one or more analogs of Q3G. In some embodiments chemical species such as andrographidine C, bisandographolide A, or andrographolide may be incorporated into a therapeutic or prophylactic composition as disclosed herein especially andrographolide.

In some embodiments, this method comprises administering an amount of kudzuisoflavone A, miquelianin, rutin, or protopseudohypericin that inhibits the replication of Marburg virus VP35 protein and/or inhibits the ability of the Marburg virus to evade host immune responses and/or inhibits the ability of VP35 to oligomerize inside a cell.

In another embodiment, the at least one of kudzuisoflavone A, miquelianin, rutin, or protopseudohypericin is administered in an amount that reduces antagonism of interferon by VP35, reduces RNA or DNA binding to VP35, reduces inhibition of interferon regulatory factor 3, and/or reduces inhibition of protein kinase R activation.

In other embodiments, the method comprises administering kudzuisoflavone A, miquelianin, rutin, and/or protopseudohypericin orally, sublingually, buccally, or topically. It was observed that all the selected phytochemicals can be orally administrated if made into a drug molecule and can be delivered through liposomal or a nanoparticle-based carrier system.

In other embodiments, the method comprises administering kudzuisoflavone A, miquelianin, rutin, and/or protopseudohypericin intraperitoneally, intravenously, intramuscularly, or by another parenteral route.

In some embodiments, white blood cells (leukocytes) such as monocytes or macrophages may be treated ex vivo or in vitro with a composition comprising kudzuisoflavone A, miquelianin, rutin, and/or protopseudohypericin, and subsequently infused or re-infused into a subject.

In other embodiments, the leukocytes such as T or B cells, neutrophiles, eosinophils, or basophils, may be treated ex vivo or in vitro with a composition comprising kudzuisoflavone A, miquelianin, rutin, and/or protopseudohypericin, and subsequently infused or re-infused into a subject.

In other embodiments, dendritic cells may be treated ex vivo or in vitro with a composition comprising kudzuisoflavone A, miquelianin, rutin, and/or protopseudohypericin, and subsequently transferred into a subject In some embodiments, the active compounds that inhibit VP35 activities may be administered to animals such as animal vectors, for example, in an edible bait.

This method may further comprise administering other antiviral agents or palliative medications. In some embodiments an active antiviral agent comprises tilorone, quinacrine, pyronaridine, favipiravir, GS-5734, or other antiviral drug to the subject.

In other embodiments, a subject infected by Marburg virus may be treated to prevent or ameliorate cytokine storm, for example, by administration of a steroid drug, like a corticosteroid, monoclonal antibodies to IL-6 or IL-1 or their receptors, such as Tocilizumab, or by extracorporeal procedures such as plasmapheresis or extracorporeal oxygenation (ECMO).

In some embodiments, the method further comprises replacing lost blood and clotting factors, administering supplemental oxygen, and/or administering water and electrolytes.

Another aspect of the disclosure is a composition comprising the kudzuisoflavone A, miquelianin, rutin, and/or protopseudohypericin in combination with a pharmaceutically acceptable carrier or excipient. This composition may further comprise other active antiviral agents such as tilorone, quinacrine, pyronaridine, favipiravir, GS-5734, or other antiviral drug.

In some embodiments, the composition is formulated for enteric or topical administration and in others it is for parenteral administration.

The composition may be formulated as a nanoparticle, a particle that encapsulates kudzuisoflavone A, miquelianin, rutin, and/or protopseudohypericin, or as a liposome.

Another aspect of the invention is a method identifying a compound that binds to VP35, including compounds structurally related to or sharing a common ring or core structures to kudzuisoflavone A, miquelianin, rutin, and/or protopseudohypericin. This method may comprise performing a virtual screening and molecular mechanics analysis combined with generalized Born surface area method (MEM-GBSA)-based pose filtering or the methods disclosed elsewhere in the specification and especially those in the Examples.

The present disclosure will now be described further with reference to the following examples, which are illustrative only and non-limiting.

Example 1

Virtual Screening and Molecular Mechanics Combined with Generalized Born Surface Area Method (MM-GBSA)-Based Pose Filtering Methodology. Virtual screening of 372 phytomolecules from Adiantum *capillus-veneris* (Southern maidenhair fern, black maidenhair fern, maidenhair fern, and venus hair fern), *Hypericum* perforatum (St John's-wort)and *Pueraria montana* (Kudzu) against the Marburg virus VP35 protein (obtained from the PDB database with PDB ID 4GHA) was conducted using the Schrodinger Glide XP docking program, coupled with pose filtering through MMGBSA analysis; see Bale, S.; Julien, J.-P.; Bornholdt, Z. A.; Kimberlin, C. R.; Halfmann, P.; Zandonatti, M. A.; Kunert, J.; Kroon, G. J.; Kawaoka, Y.; MacRae, I. J. Marburg Virus VP35 Can Both Fully Coat the Backbone and Cap the Ends of DsRNA for Interferon Antagonism. 2012. 17. Friesner, R. A.; Murphy, R. B.; Repasky, M. P.; Frye, L. L.; Greenwood, J. R.; Halgren, T. A.; Sanschagrin, P. C.; Mainz, D.T. Extra Precision Glide: Docking and Scoring Incorporating a Model of Hydrophobic Enclosure for Protein-Ligand Complexes. Journal of medicinal chemistry 2006, 49, 6177-6196. Schrodinger Release 2020-4: Glide, Schrodinger, LLC, New York, NY, 2020. Schrödinger Release 2020-4: Prime, Schrödinger, LLC, New York, NY, 2020—each incorporated herein by reference in its entirety.

This methodology involved several steps. First, the protein structure was prepared using Schrodinger's Protein Preparation Wizard, which included adding missing atoms, assigning bond orders, and optimizing hydrogen bonds. The prepared protein structure was then used to generate a receptor grid around the binding site predicted using CASTp server; see Schrodinger Release 2020-4: Protein Preparation Wizard; Epik, Schrodinger, LLC, New York, NY, 2020; Impact, Schrodinger, LLC, New York, NY; Prime, Schrodinger, LLC, New York, NY, 2020. 2020. Tian, W.; Chen, C.; Lei, X.; Zhao, J.; Liang, J. CASTp 3.0*: Computed Atlas of Surface Topography of Proteins*. Nucleic Acids Research 2018, 46, W363-W367, doi:10.1093/nar/gky473—each incorporated herein by reference in its entirety.

The 372 phytomolecules, obtained from the IMPPAT database, were prepared using LigPrep, which generated different protonation states, tautomers, and ionization states; see Mohanraj, K.; Karthikeyan, B.S.; Vivek-Ananth, R. P.; Chand, R. P. B.; Aparna, S. R.; Mangalapandi, P.; Samal, A. IMPPAT: *A Curated Database of Indian Medicinal Plants, Phytochemistry And Therapeutics*. SC1REP 2018, 8, 4329, doi:10.1038/s41598-018-22631-z. Chen, I.-J.; Foloppe, N. *Drug-like Bioactive Structures and Conformational Coverage with the LigPrep ConfGen Suite: Comparison to Programs MOE and Catalyst*. Journal of chemical information and modeling 2010, 50, 822-839. LigPrep Schrödinger Release 2020-4: LigPrep, Schrödinger, LLC, New York, NY, 2020—each incorporated herein by reference in its entirety.

Afterward, the prepared ligands were docked into the binding site of the protein using Glide XP, which employed a scoring algorithm to evaluate the binding affinity of each molecule.

The obtained poses were filtered based on the basis of their MMGBSA values, selecting the top-scoring compounds for later analysis.

The stability and binding affinity of the protein-ligand complexes were revealed by this study. The substances with the best binding free energies were chosen as potential hits for additional research. Schrodinger's Maestro software, which allows for the analysis of many sorts of interactions, was used to analyze the interactions between the chosen chemicals and the VP35 protein; Schrodinger Release 2020-4: Maestro, Schrödinger, LLC, New York, NY, 2020. For this work, myricetin, an Ebola Virus VP35 Protein from *Limonium* morisianum, was used as a reference molecule.

Results: Virtual screening and AIGBSA-based pose filtering. Virtual screening of 372 phytomolecules was performed against the Marburg virus VP35 protein to identify potential inhibitors. The compounds were screened using molecular docking simulations, and the binding affinities were evaluated based on docking scores. The results revealed a subset of compounds with promising binding interactions and high predicted affinity towards the VP35 protein. The MMGBSA calculations were performed to filter the best-docked poses based on delta G binding energy values. The best binding poses of the top four phytomolecules (kudzuisoflavone A, miquelianin, rutin, and protopseudohypericin) were selected to investigate their binding interactions with the Marburg virus VP35 protein. The chemical structures of these four compounds are shown in FIGS. 1A-1D. The docking score and delta G binding score of the four selected compounds are given in Table 1.

TABLE 1

List of top four selected compound names, IMPPAT ID, source, docking score, and their MMGBSA delta G free binding energy in complex with Marburg virus VP35 protein.

| Source | IMPPAT ID | Compound Name | Docking score (kcal/mol) | MMGBSA/ Delta G (kcal/mol) |
|---|---|---|---|---|
| *Pueraria montana* | IMPHY006572 | kudzuisoflavone A | −3.097 | −43.69 |
| *Adiantum capillus-veneris* | IMPHY011618 | miquelianin | −4.078 | −42.00 |
| *Hypericum perforatum* | IMPHY015047 | rutin | −7.333 | −40.63 |
| *Hypericum perforatum* | IMPHY006126 | Protopseudohypericin | −3.051 | −40.63 |
| *Limonium morisianum* | IMPHY005471 | myricetin (reference molecule) | −4.534 | −33.57 |

Kudzuisoflavone A exhibited a binding mode where it formed hydrogen bonds with amino acid residues SER-270, ASN-306 and TRP-313. ARG-271 and LYS-328 formed pi-cation interactions, while other neighboring residues were also establishing favorable hydrophobic contacts within the binding site of the VP35 protein. The calculated free binding energy for kudzuisoflavone A was −43.69 kcal/mol, indicating a strong binding affinity to the VP35 protein. Miquelianin demonstrated a binding mode characterized by the formation of strong hydrogen bonds with residues GLU-260, ASN-261, GLN-263, ARG-271, and ILE-329, along with significant hydrophobic interactions. The free binding energy for miquelianin was −42.0 kcal/mol, suggesting favorable interactions with the VP35 protein. Rutin showed docking results with hydrogen bonds formed with residues THR-267, SER-270, ARG-271, LYS-328, and ILE-329, as well as hydrophobic contacts with surrounding residues, while LYS-311 formed salt bridge contact. The calculated binding free energy for rutin was −40.63 kcal/mol, indicating a moderately strong binding affinity. Protopseudohypericin exhibited a binding mode involving hydrogen bonds with residues ARG-301 and LYS-311, while TRP-313 formed four pi-pi interactions. The calculated binding free energy for protopseudohypericin was also −40.63 kcal/mol, indicating a moderately strong binding affinity. See FIGS. 2A-2H.

Figure 2A:
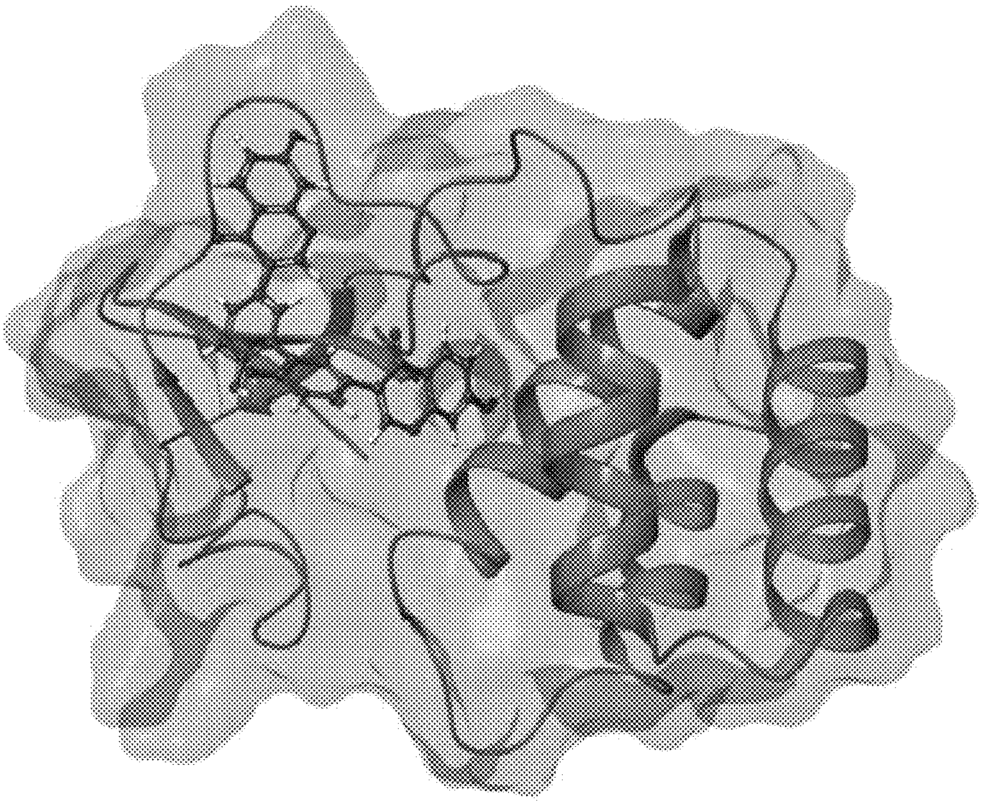
FIGS. 2A-2J describe interaction energy of the four compounds in both 2D and 3D diagrams. See also Table 1 which shows the docking scores and free binding energy of all tested compounds during interaction with the target protein and explains these interactions.
Figure 2B:
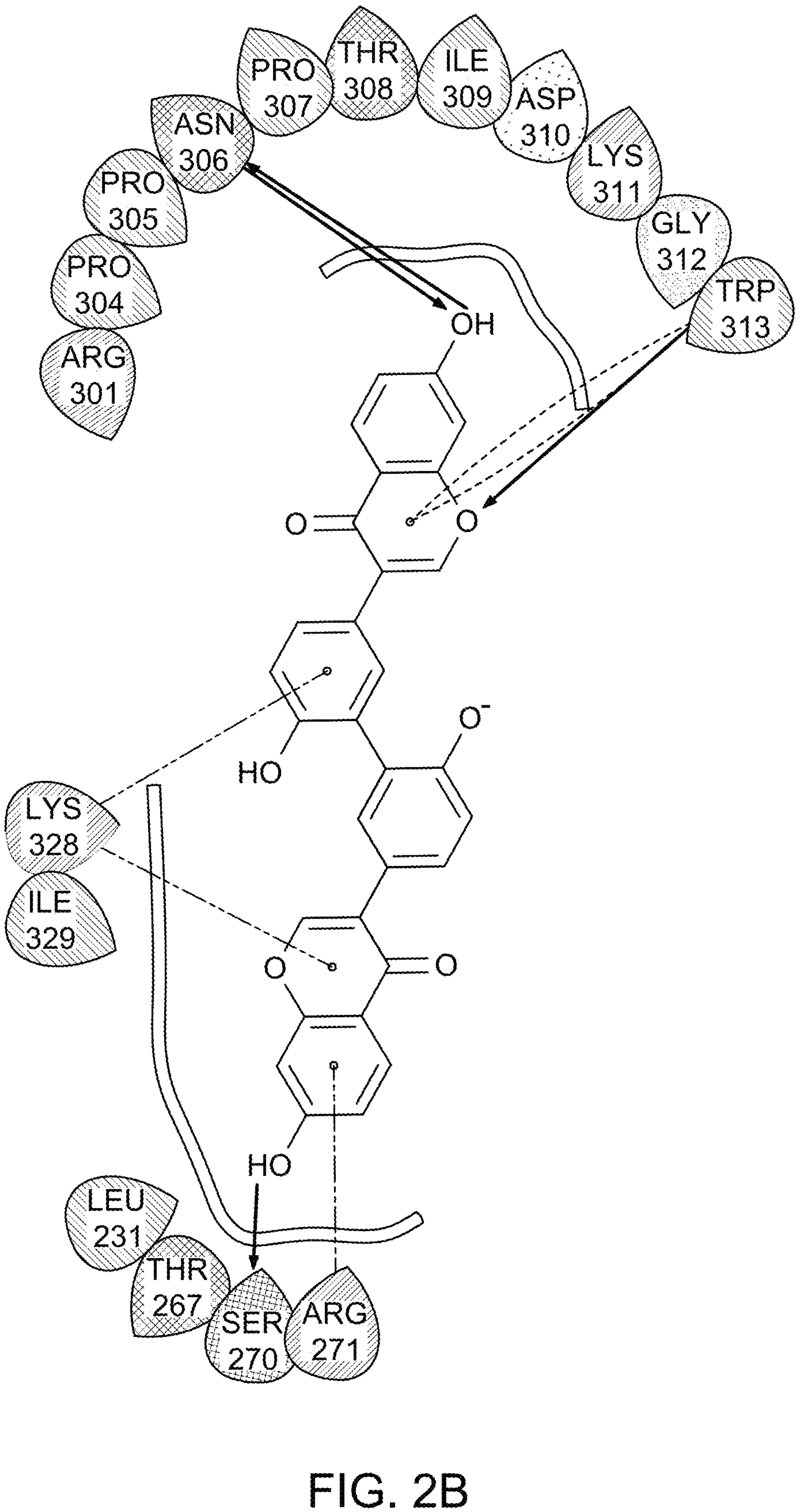
Figure 2C:
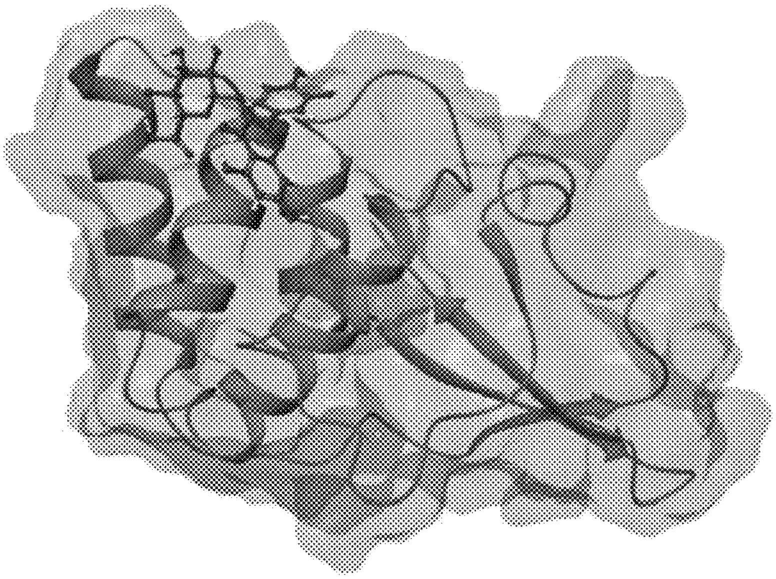
Figure 2D:
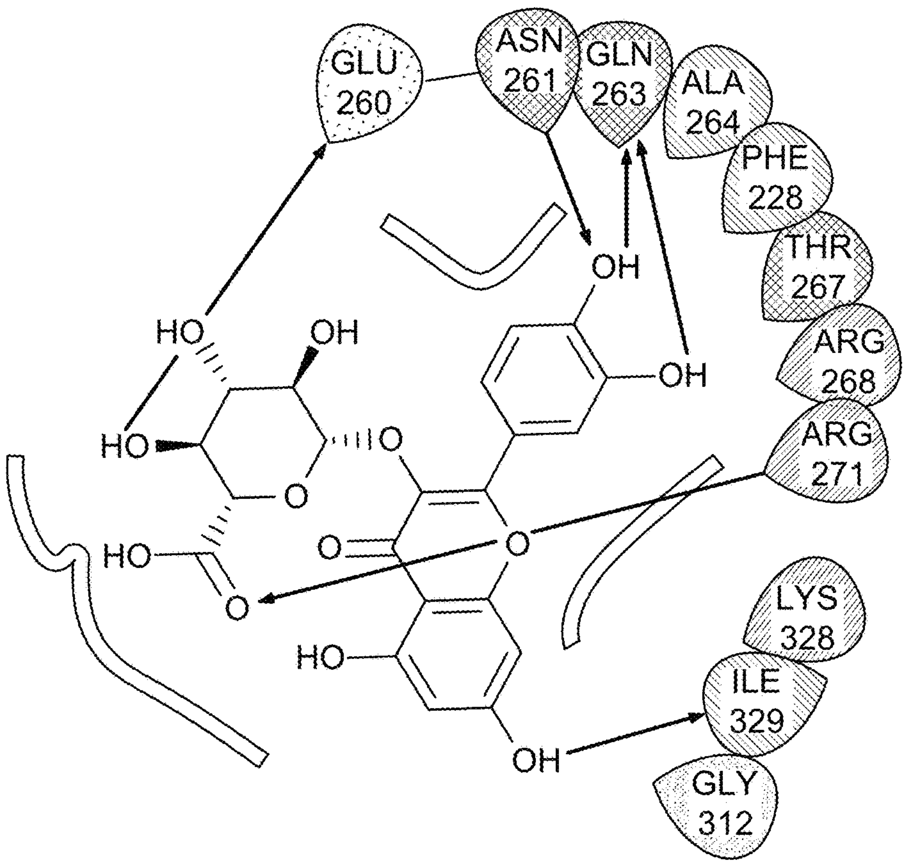
Figure 2E:
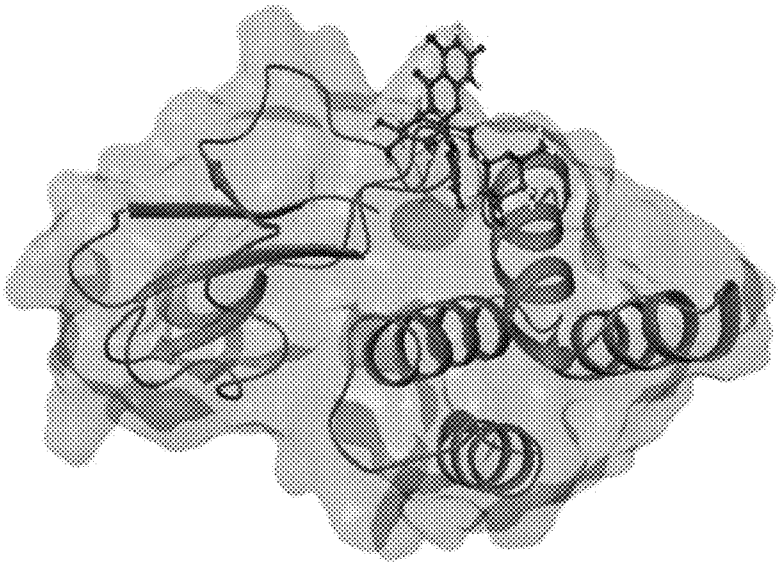
Figure 2F:
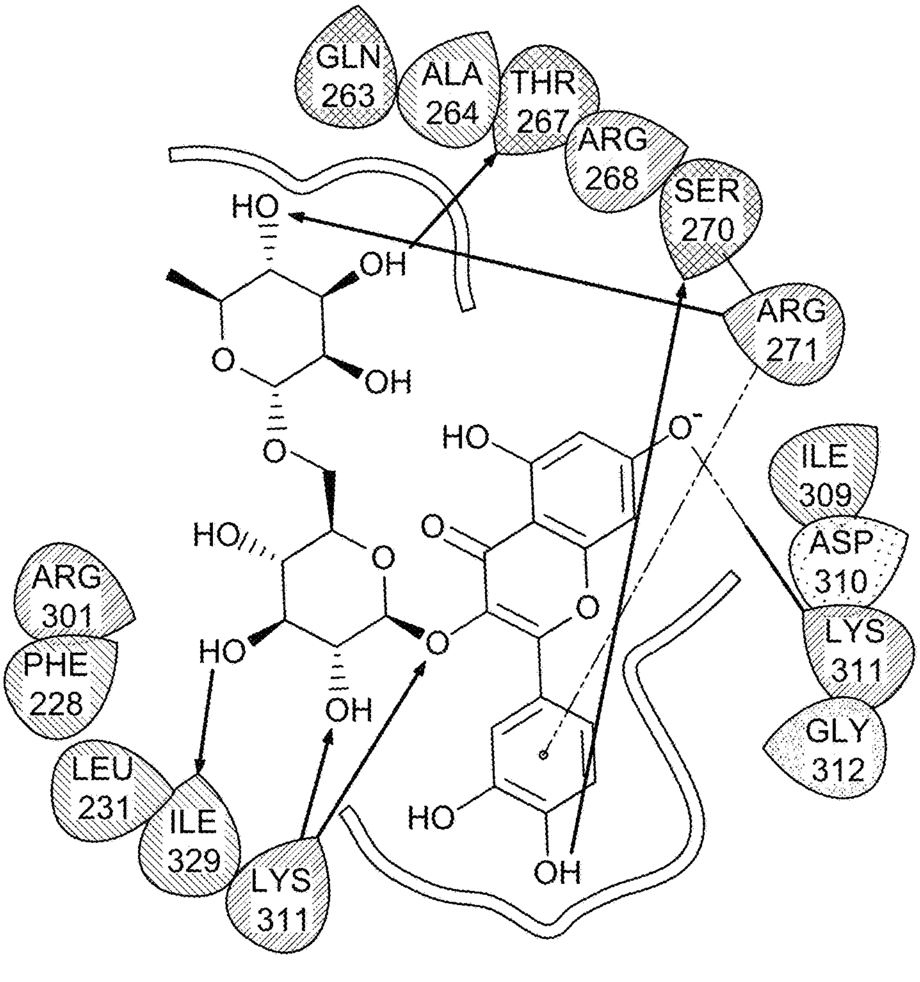
Figure 2G:
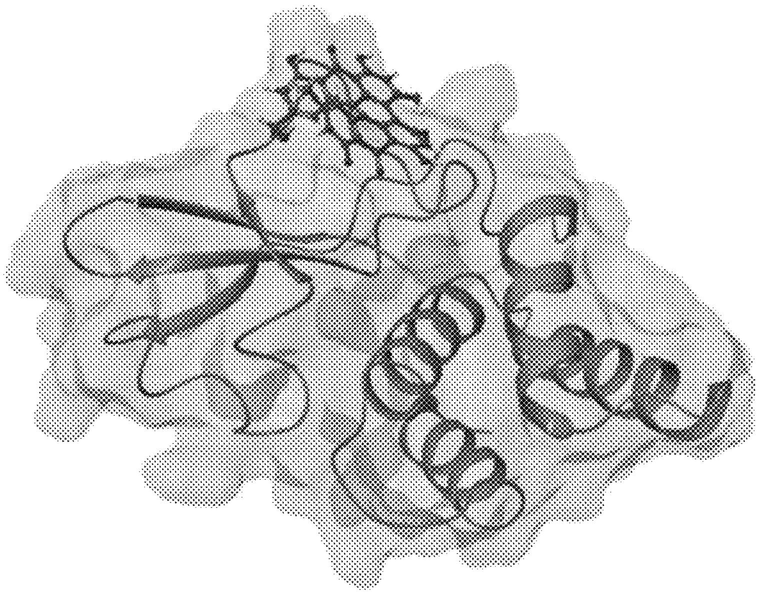
Figure 2H:
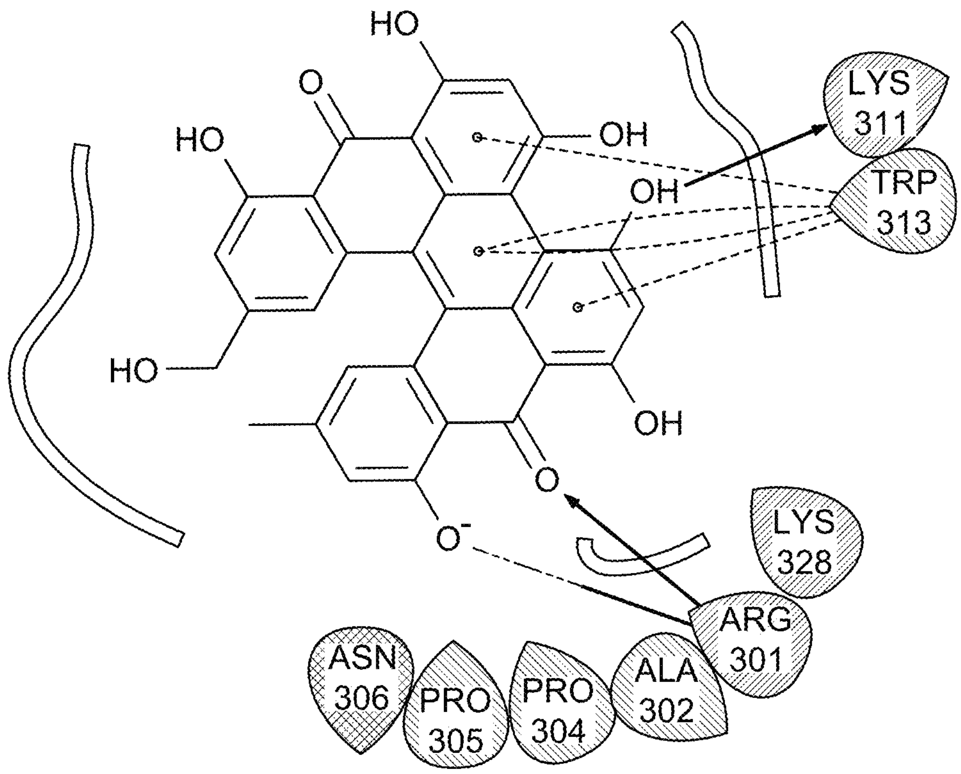
Figure 2I:
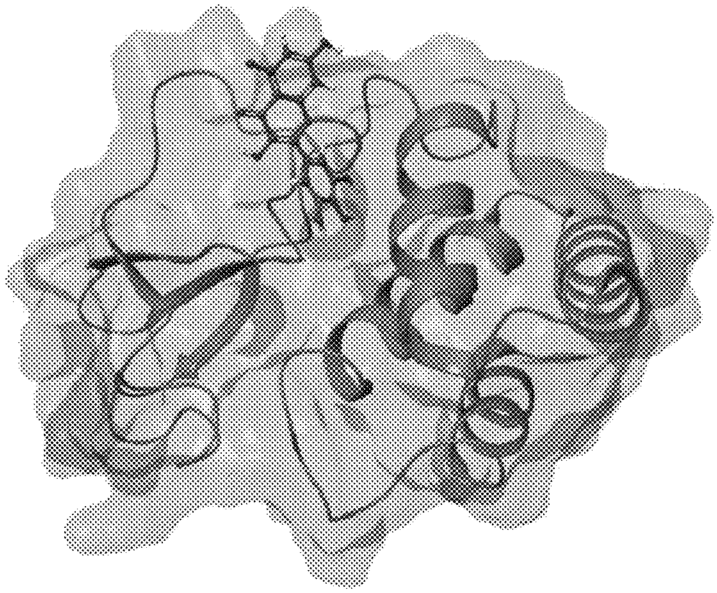
Figure 2J:
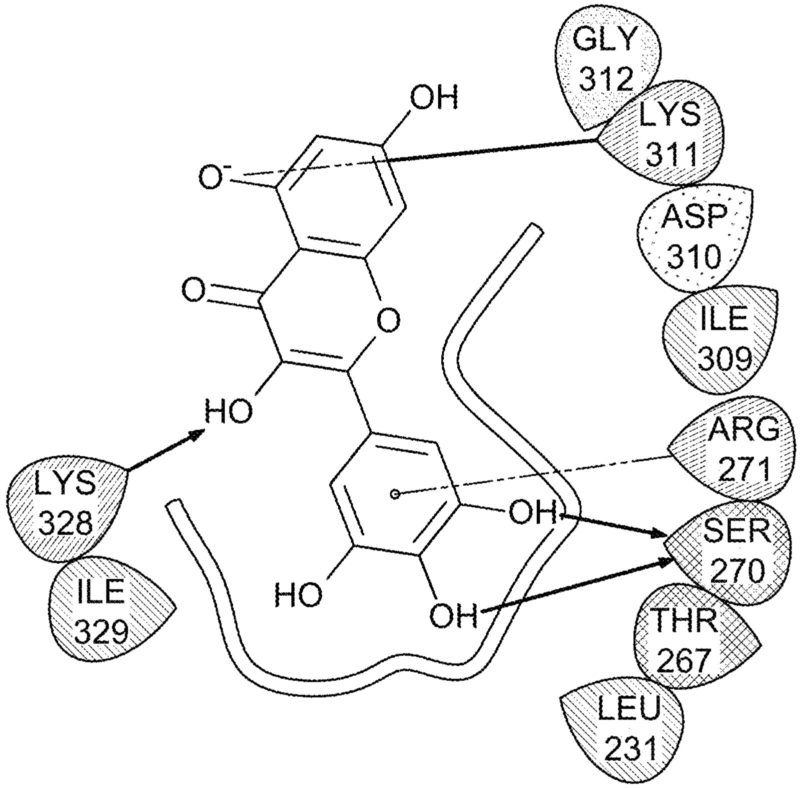
Figure 3A:
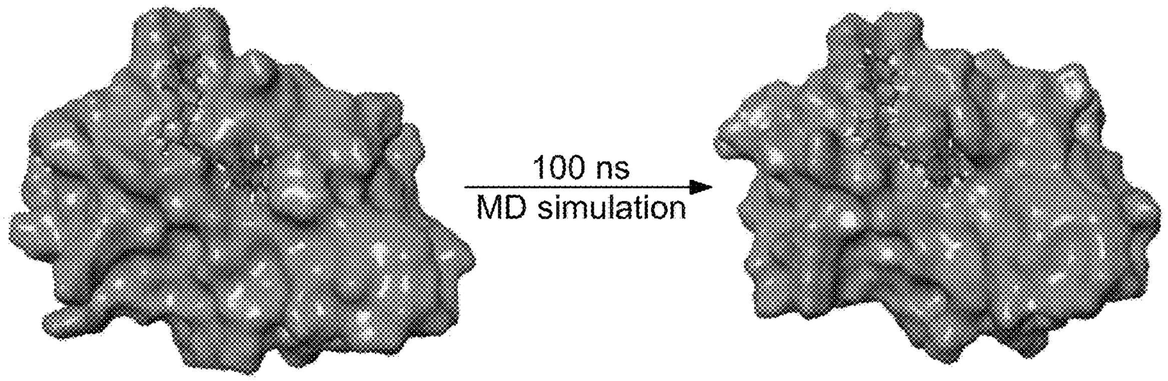
FIG. 3A. First and last pose analysis of the docked phytochemical compound kudzuisoflavone A extracted from the simulation trajectories.
Figure 3B:
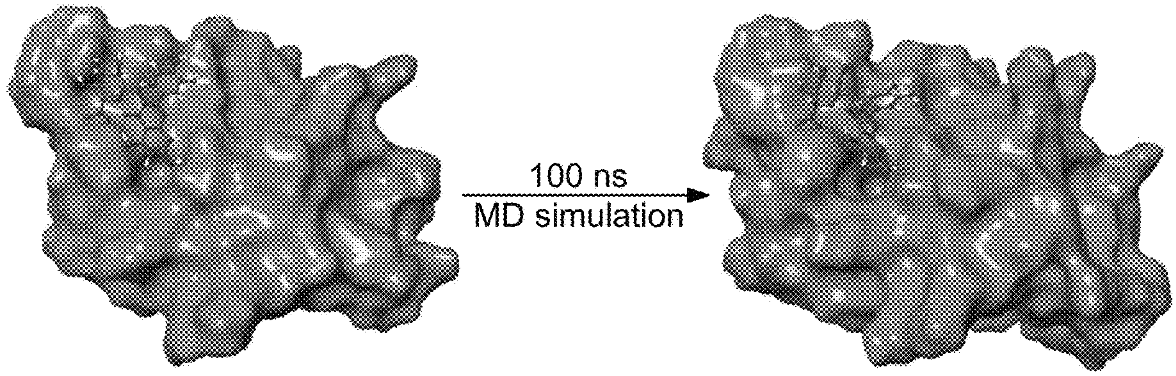
FIG. 3B. First and last pose analysis of the docked phytochemical compound miquelianin extracted from the simulation trajectories.
Figure 3C:
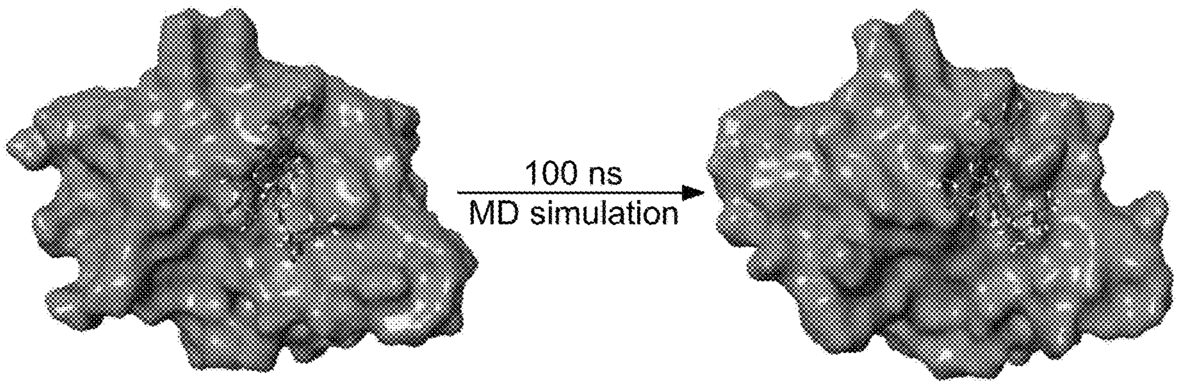
FIG. 3C. First and last pose analysis of the docked phytochemical compound rutin extracted from the simulation trajectories.
Figure 3D:
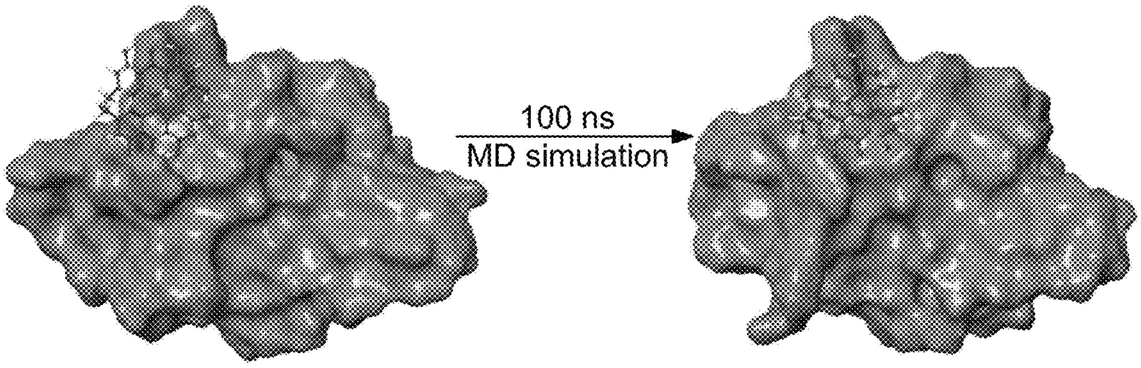
FIG. 3D. First and last pose analysis of the docked phytochemical compound protopseudohypericin extracted from the simulation trajectories.
Figure 3E:
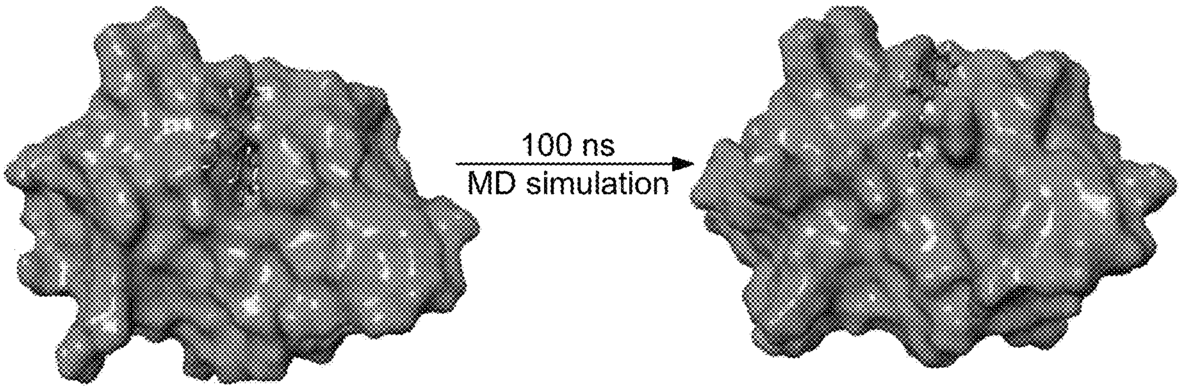
FIG. 3E. First and last pose analysis of the docked phytochemical reference compound myricetin extracted from the simulation trajectories.
Figure 4A:
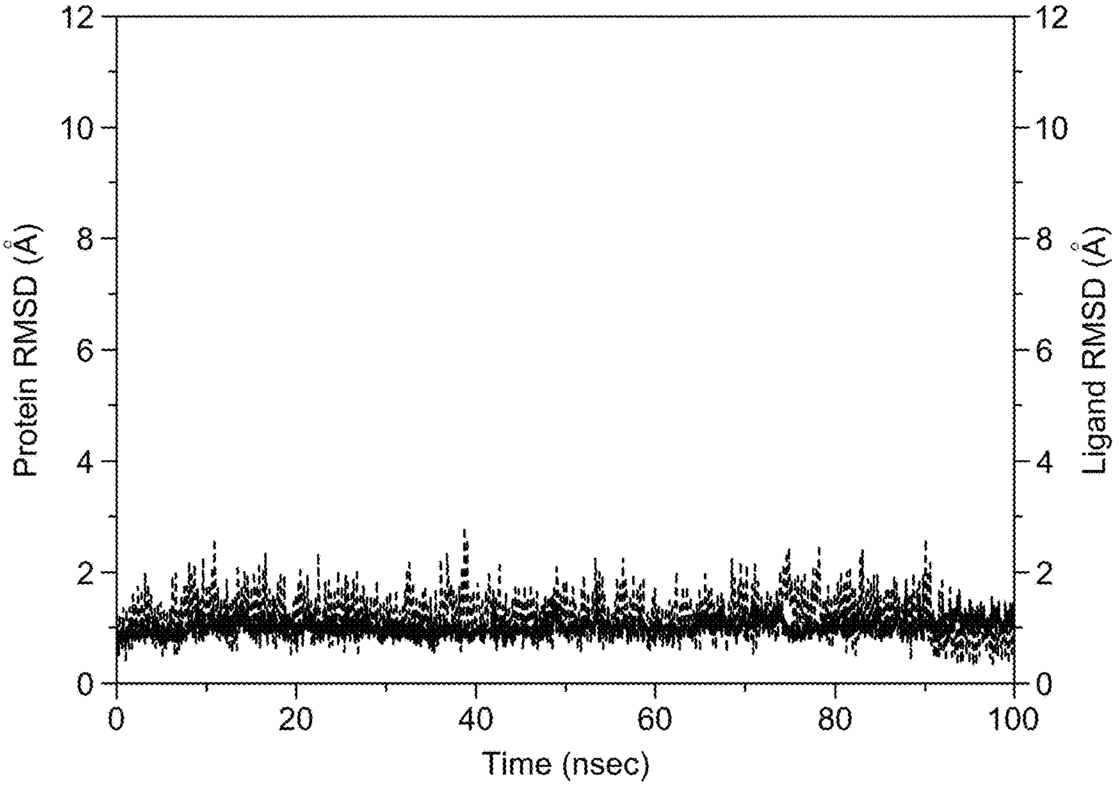
FIG. 4A. RMSD plot of the docked phytochemical compound viz kudzuisoflavone A.
Figure 4B:
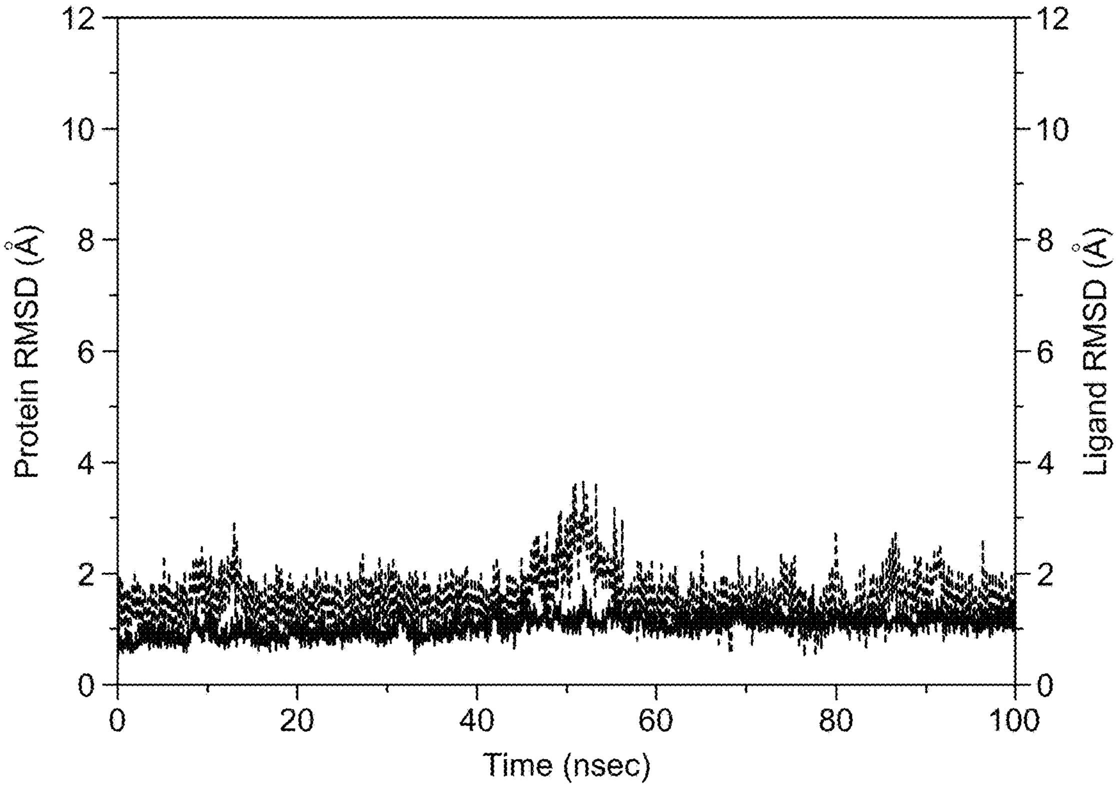
FIG. 4B. RMSD plot of the docked phytochemical compound viz miquelianin.
Figure 4C:
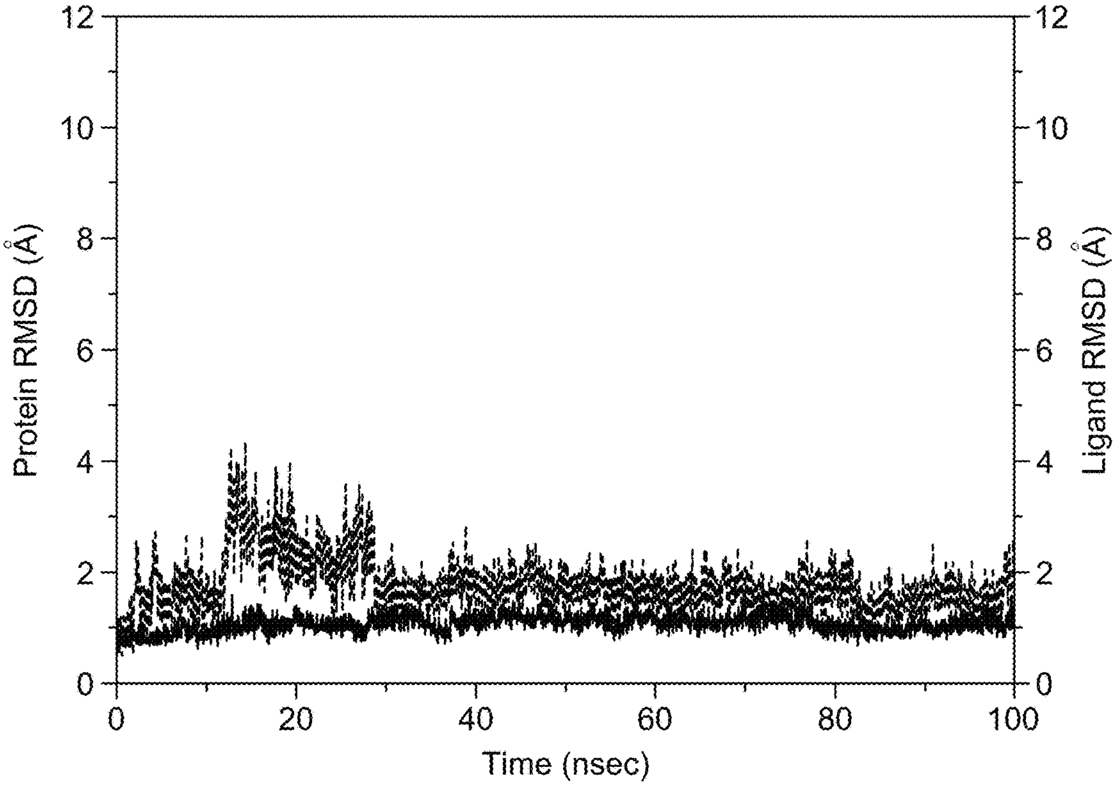
FIG. 4C. RMSD plot of the docked phytochemical compound viz rutin.
Figure 4D:
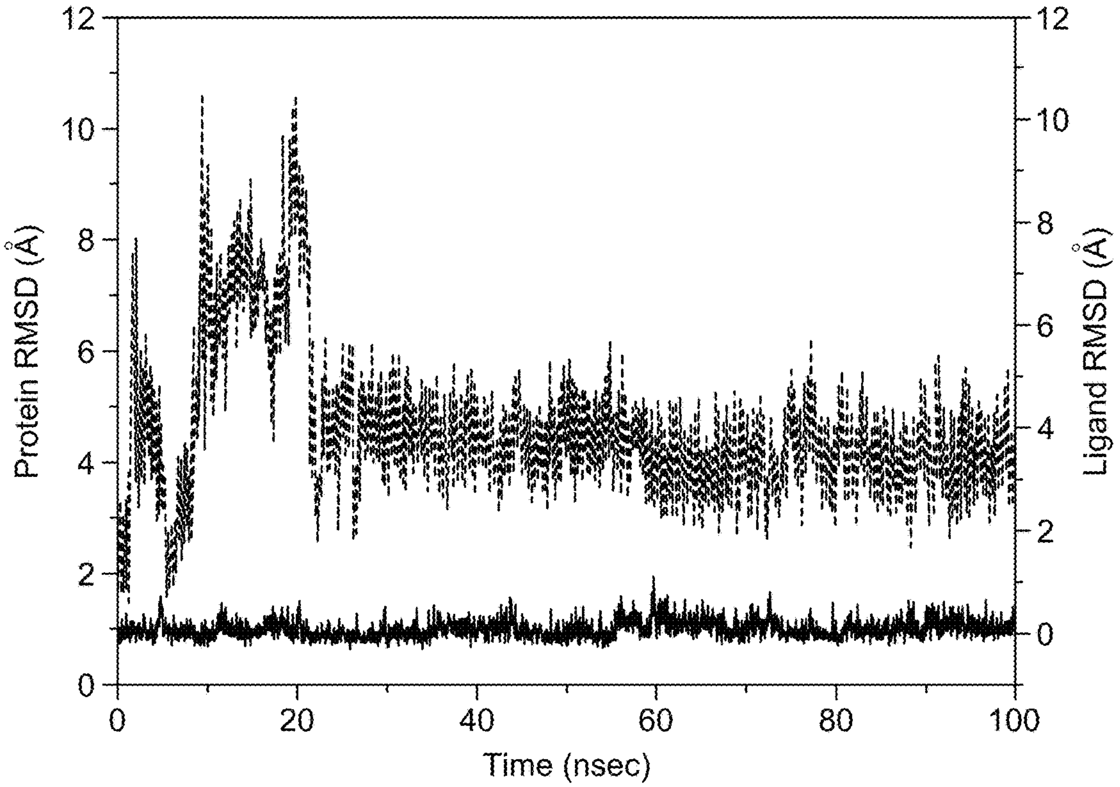
FIG. 4D. RMSD plot of the docked phytochemical compound viz protopseudohypericin.
Figure 4E:
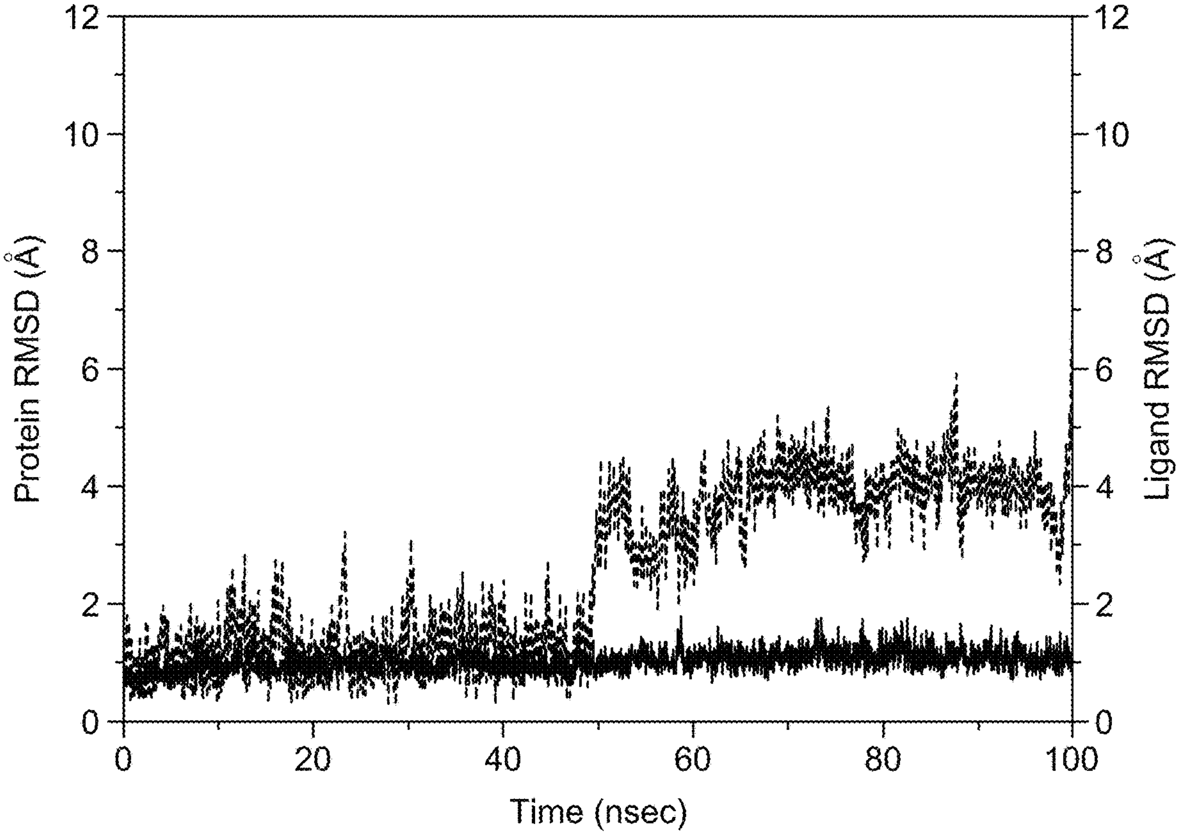
FIG. 4E. plot of the docked phytochemical compound viz myricetin. A smaller RMSD typically indicates a more stable complex, but in some systems, a complex with a higher RMSD value may be acceptable as it may naturally exhibit more structural flexibility.
Figure 5A:
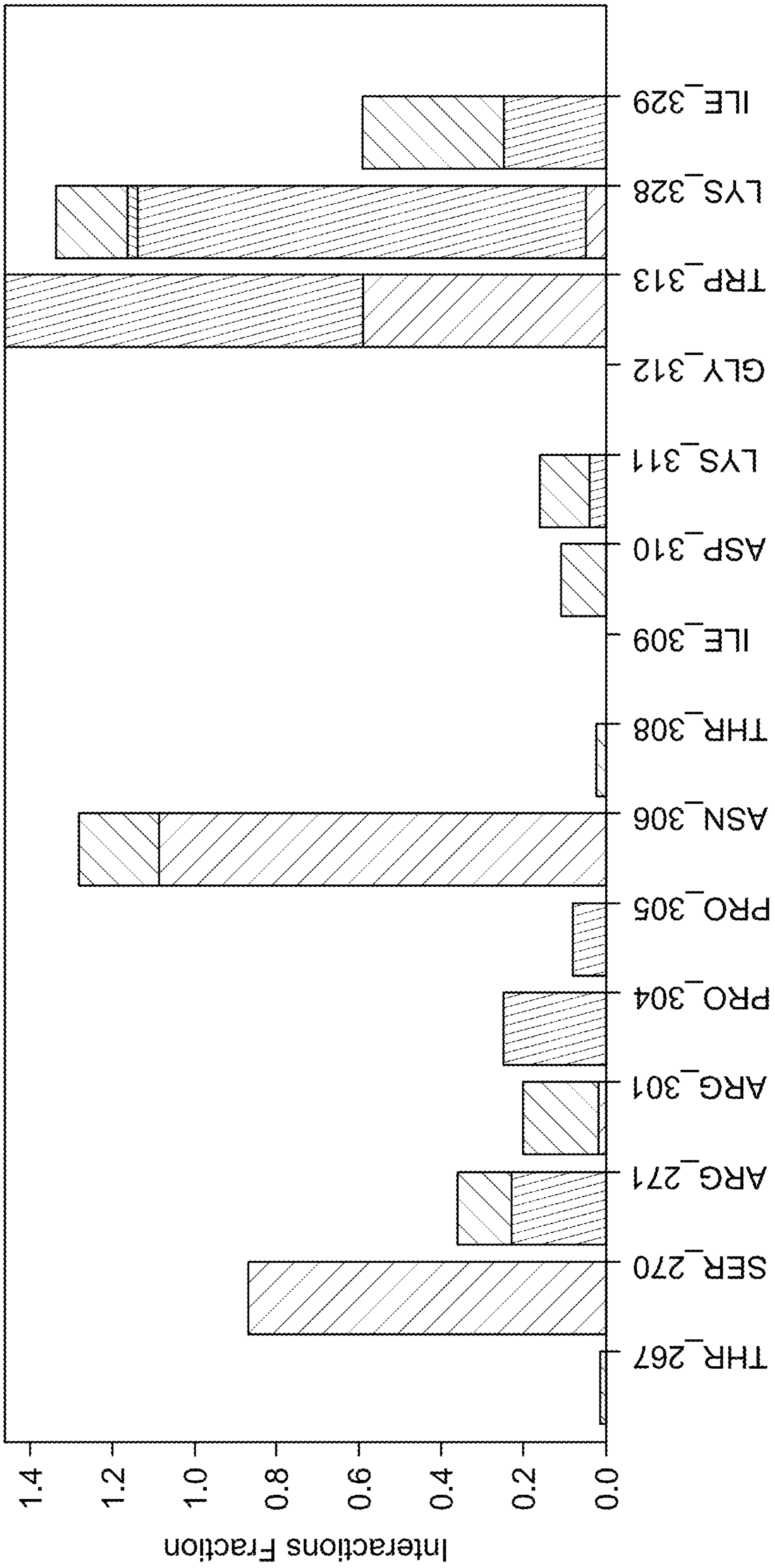
FIG. 5A. Protein-ligand interaction monitored throughout the MD simulation of kudzuisoflavone A.
Figure 5B:
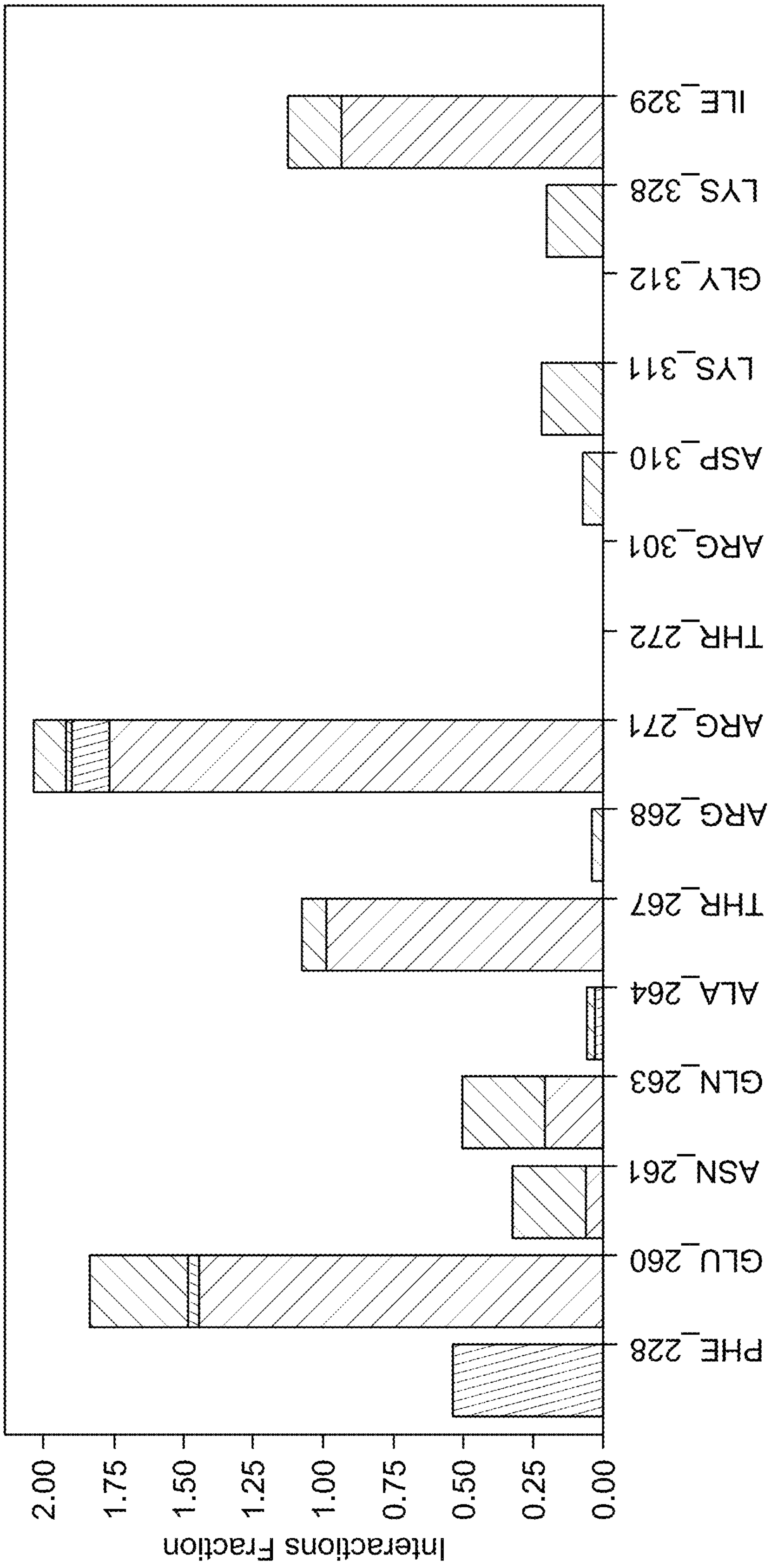
FIG. 5B. Protein-ligand interaction monitored throughout the MD simulation of miquelianin.
Figure 5C:
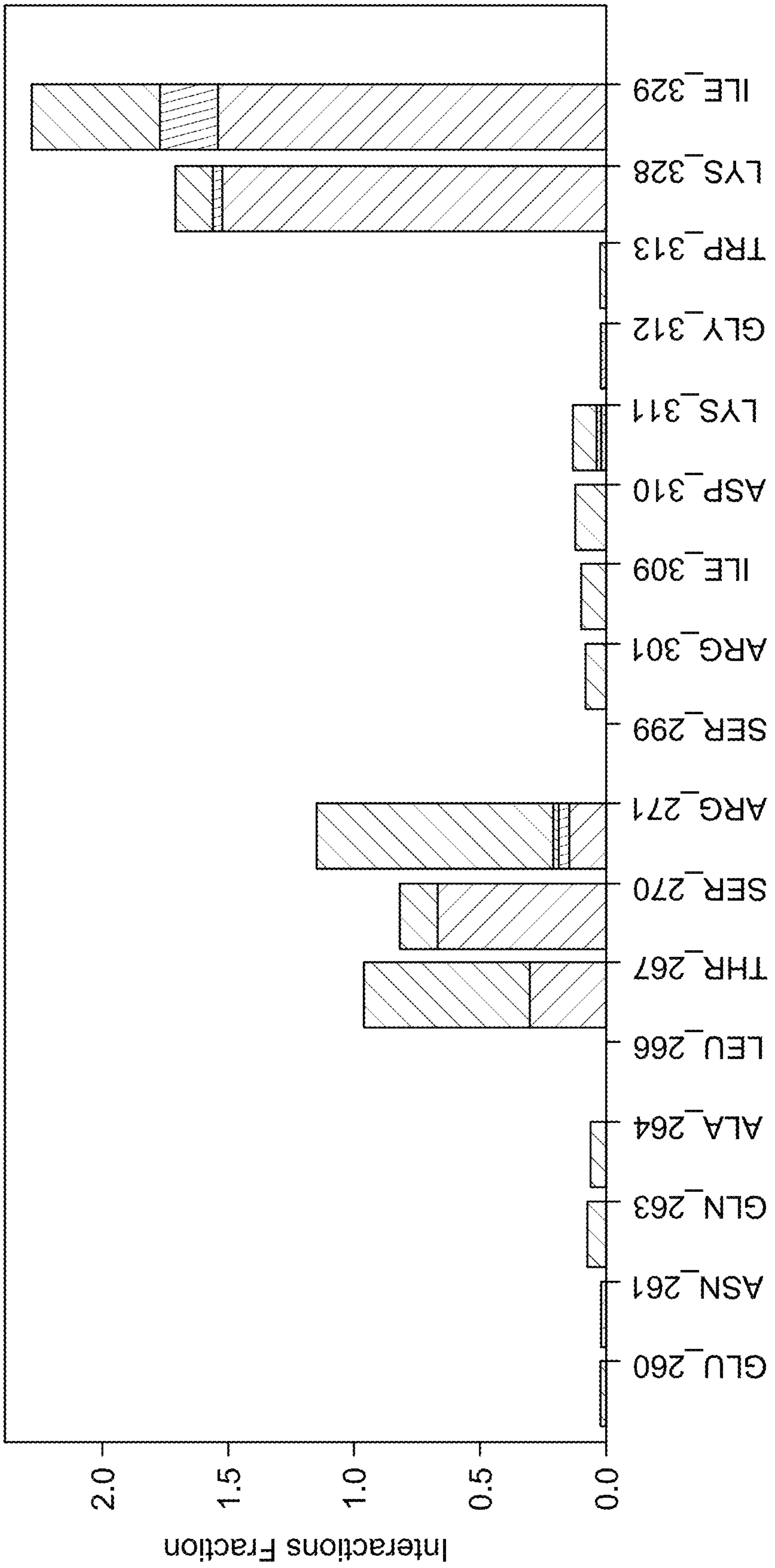
FIG. 5C. Protein-ligand interaction monitored throughout the MD simulation of rutin.
Figure 5D:
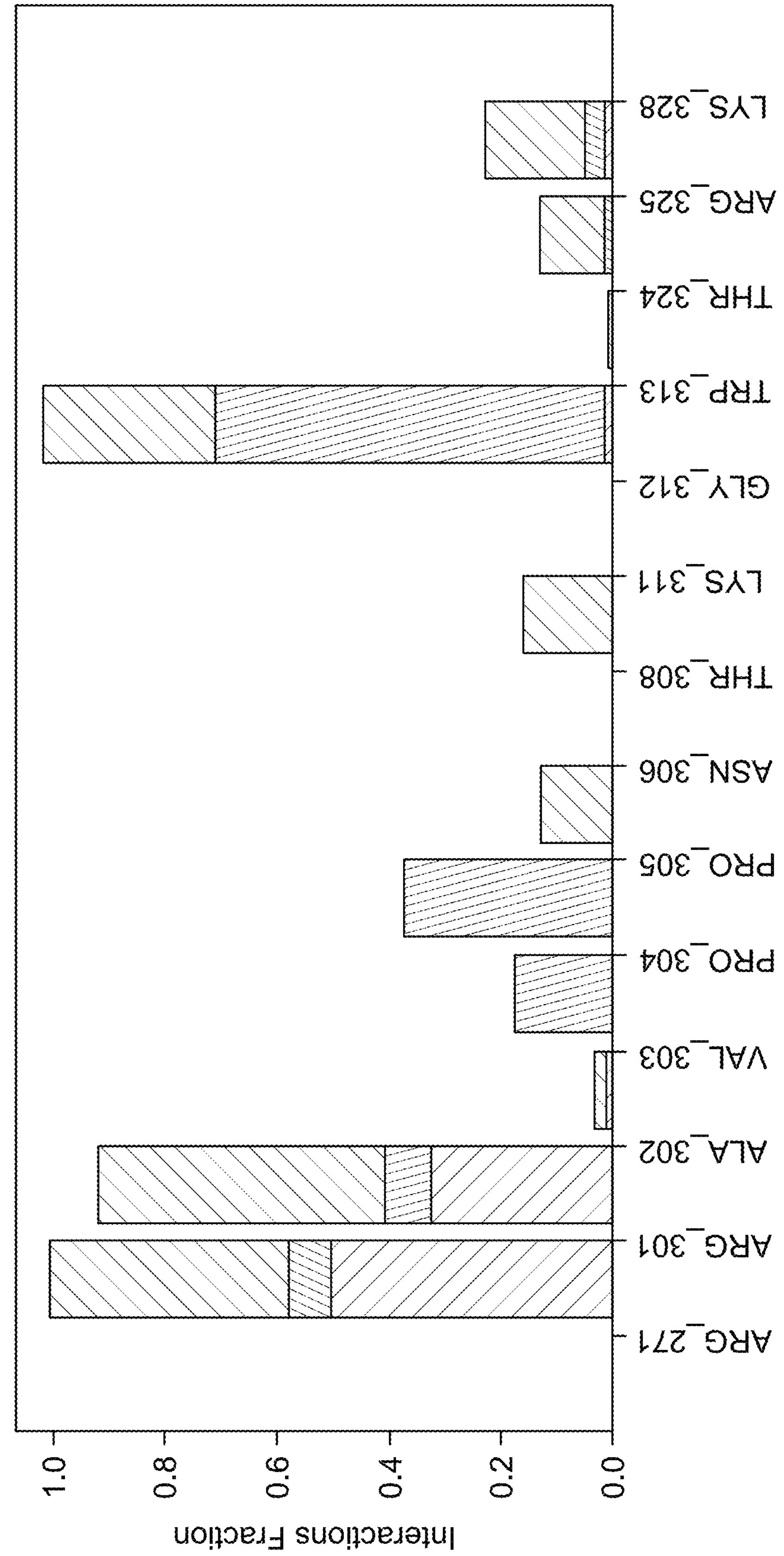
FIG. 5D. Protein-ligand interaction monitored throughout the MD simulation of protopseudohypericin.
Figure 5E:
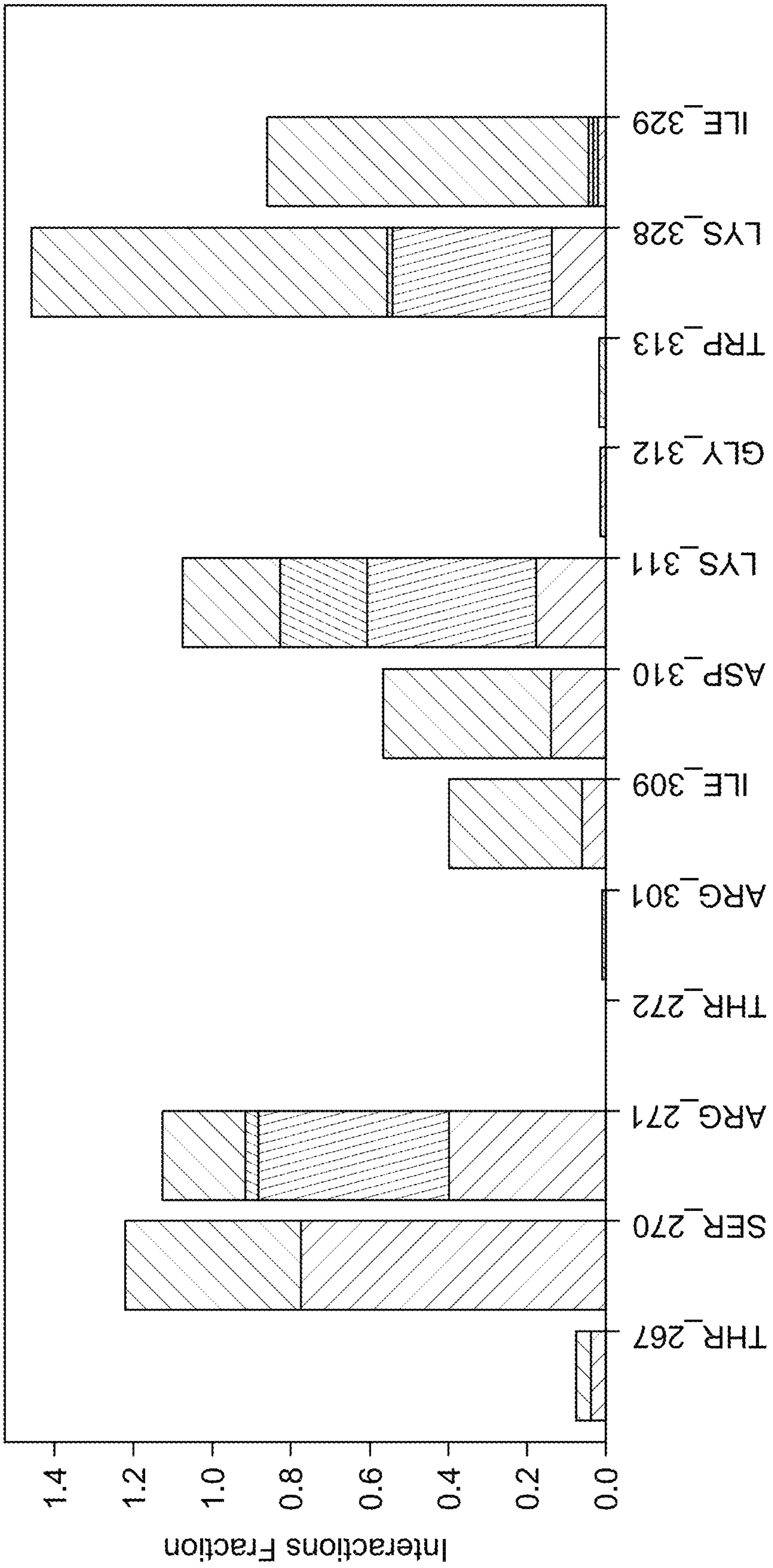
FIG. 5E. Protein-ligand interaction monitored throughout the MD simulation of myricetin.
Figure 6A:
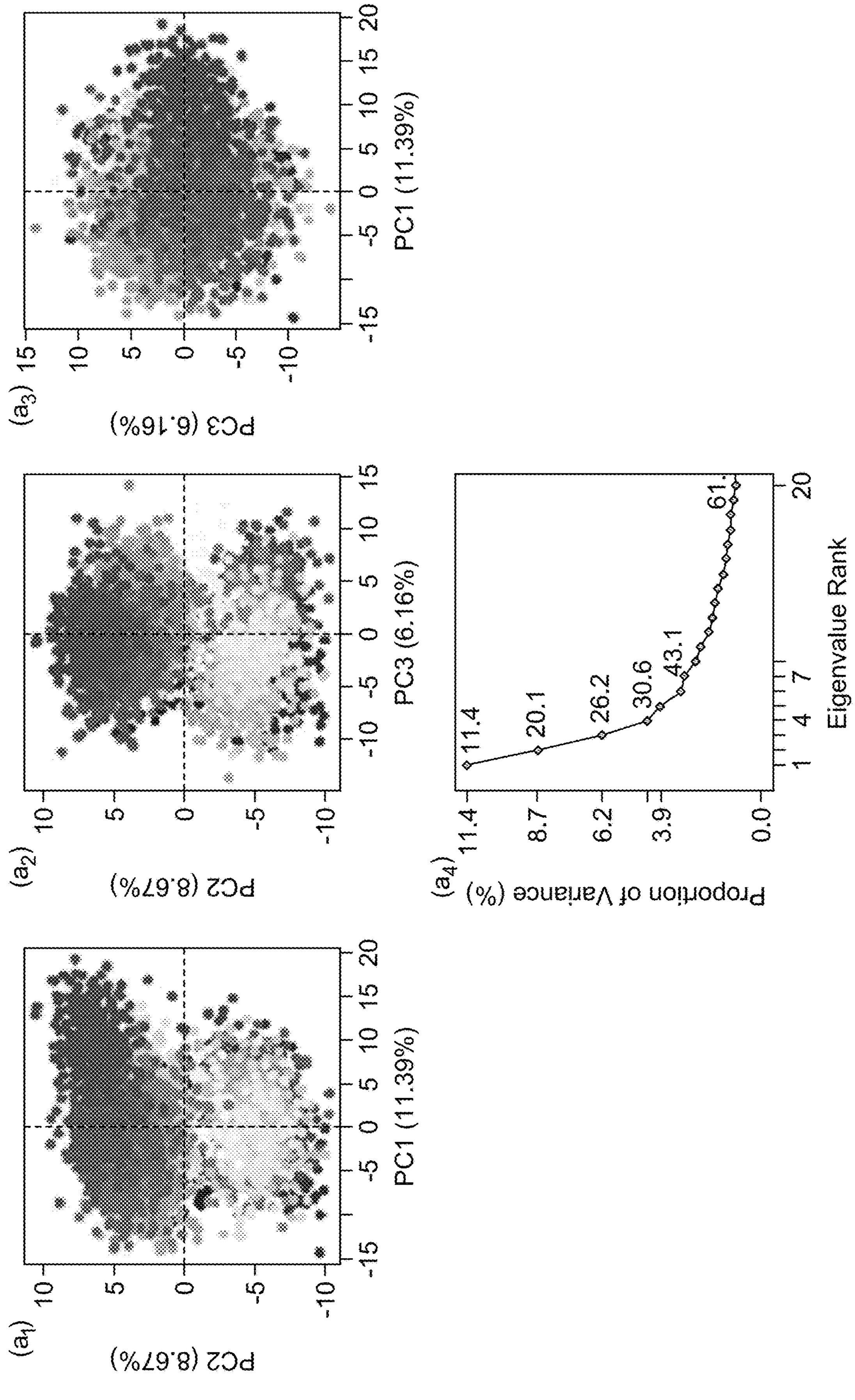
FIG. 6A. PCA analysis of the docked phytochemical compound viz kudzuisoflavone A. Subpanels $6a_1$-$6a_3$ are PCA plots; panel $6a_4$ is a scree plot.
Figure 6B:
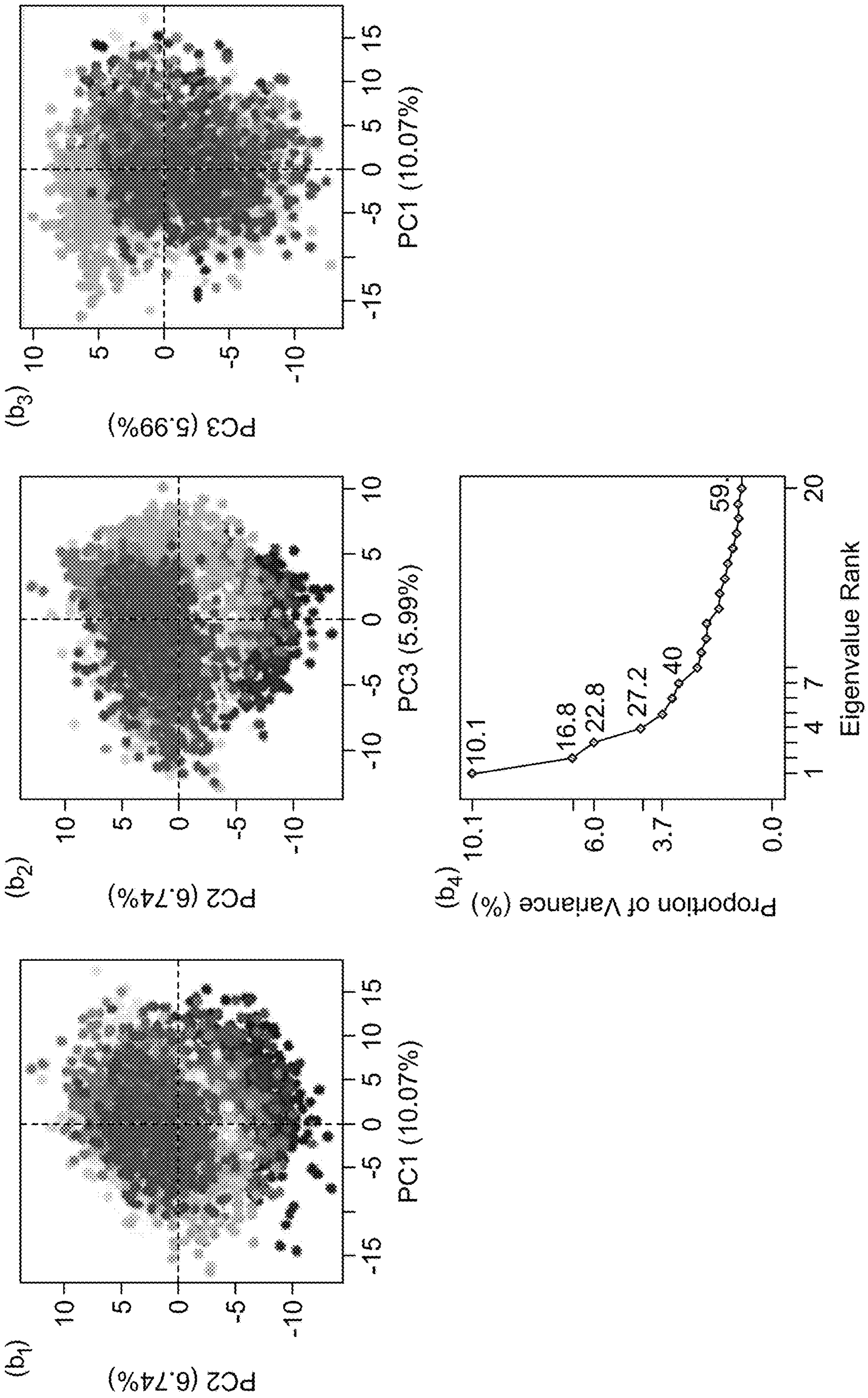
FIG. 6B. PCA analysis of the docked phytochemical compound viz miquelianin. Subpanels $6b_1$-$6b_3$ are PCA plots; panel $6b_4$ is a scree plot.
Figure 6C:
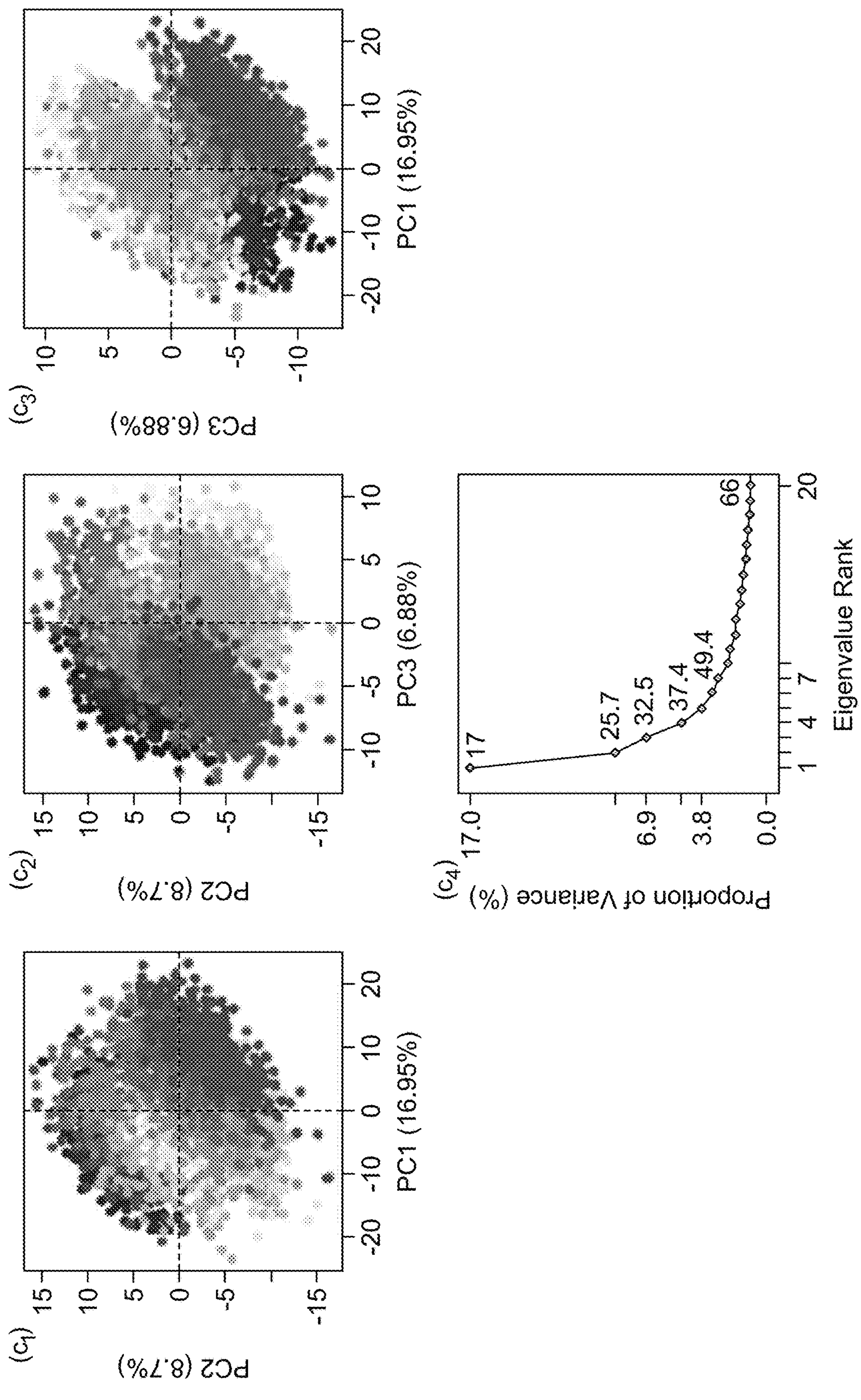
FIG. 6C. PCA analysis of the docked phytochemical compound viz rutin. Subpanels 6ci-6c3 are PCA plots; panel 6c4 is a scree plot.
Figure 6D:
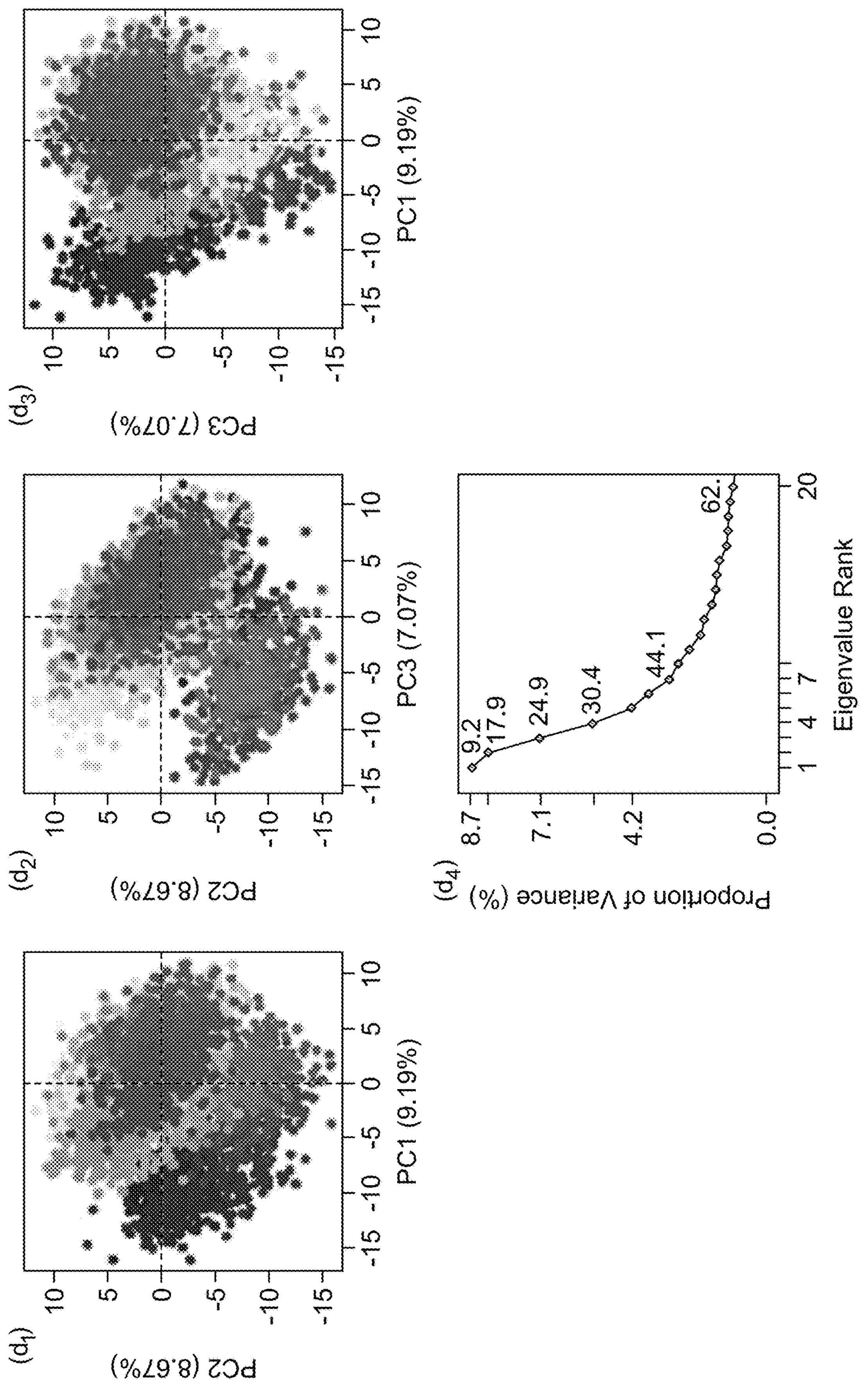
FIG. 6D. PCA analysis of the docked phytochemical compound viz protopseudohypericin. Subpanels 6di-6d3 are PCA plots; panel 6d4 is a scree plot.
Figure 6E:
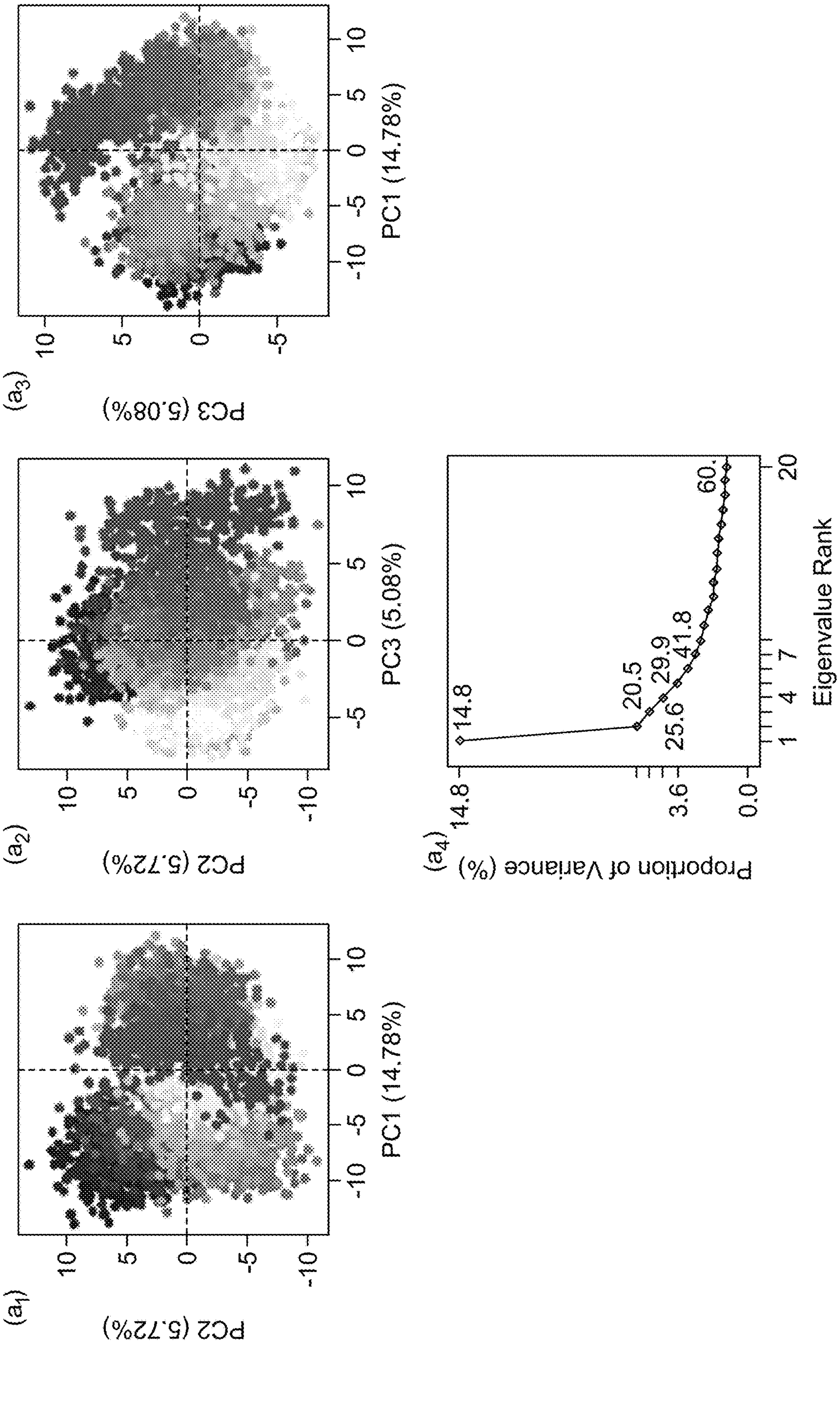
FIG. 6E. PCA analysis of the docked phytochemical compound viz myricetin. Subpanels $6a_1$-$6a_3$ are PCA plots; panel $6a_4$ is a scree plot.
Figure 7A:
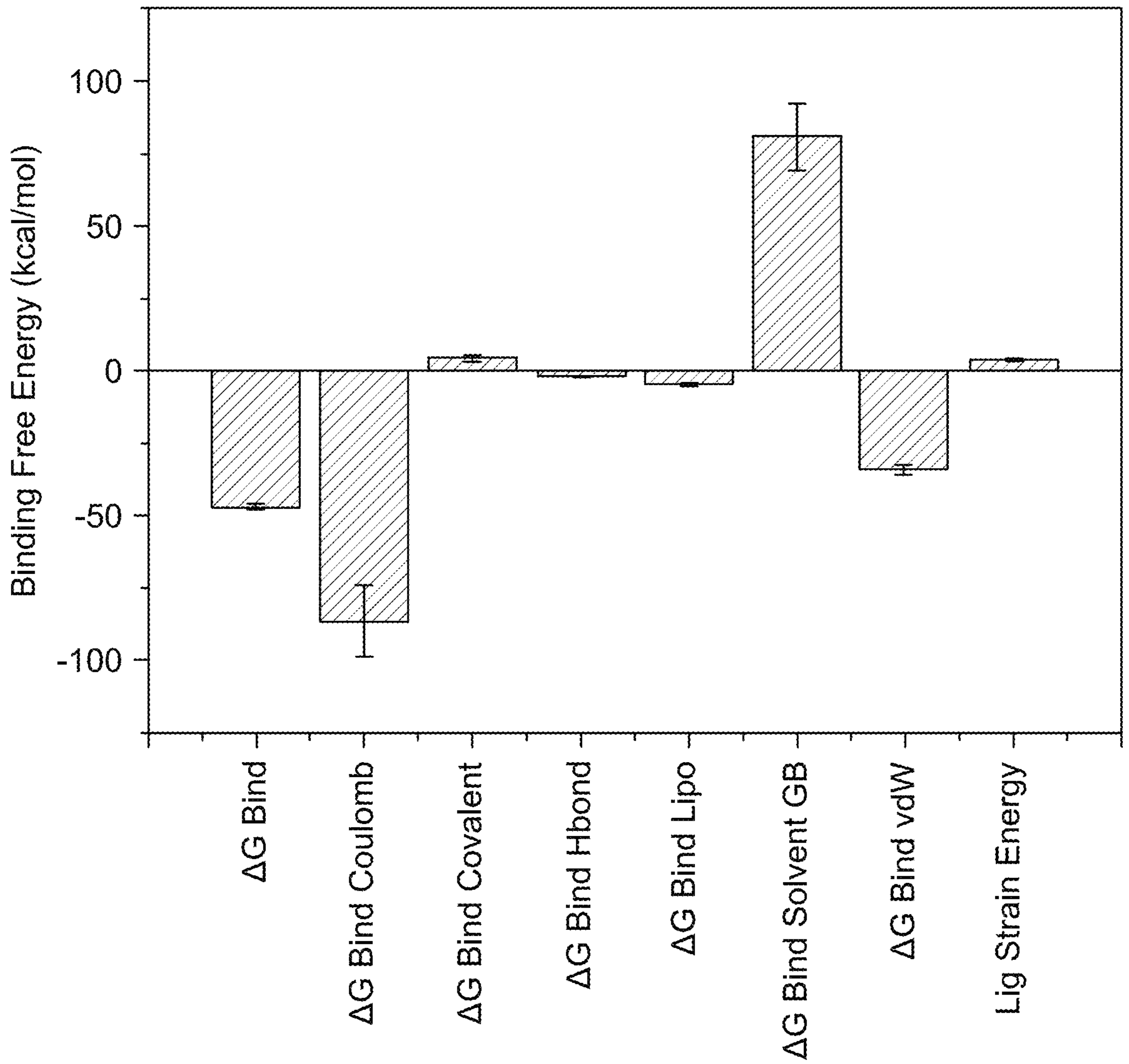
FIG. 7A. Binding free energy analysis of the docked phytochemical compound viz a) kudzuisoflavone A.
Figure 7B:
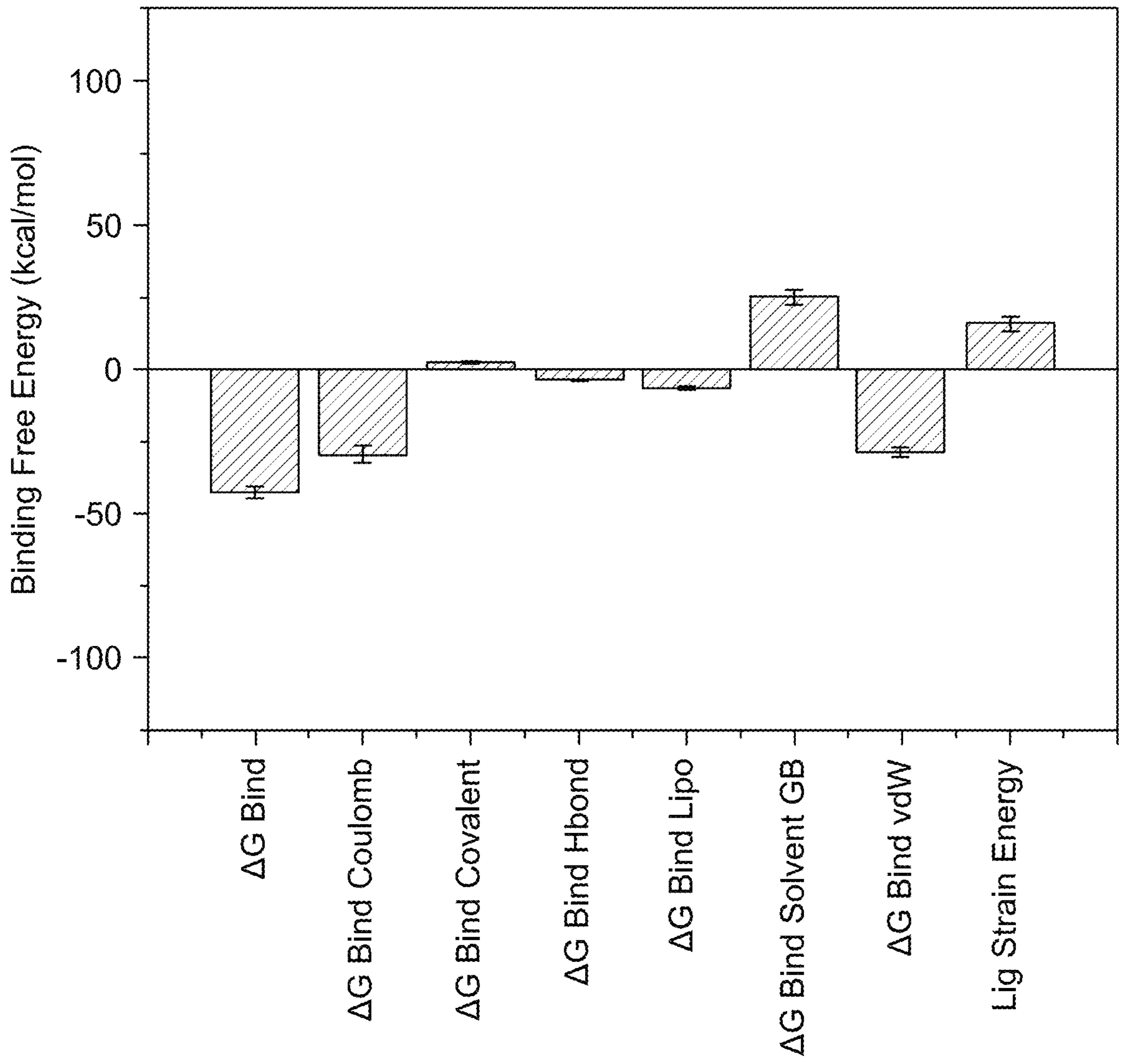
FIG. 7B. Binding free energy analysis of the docked phytochemical compound viz miquelianin.
Figure 7C:
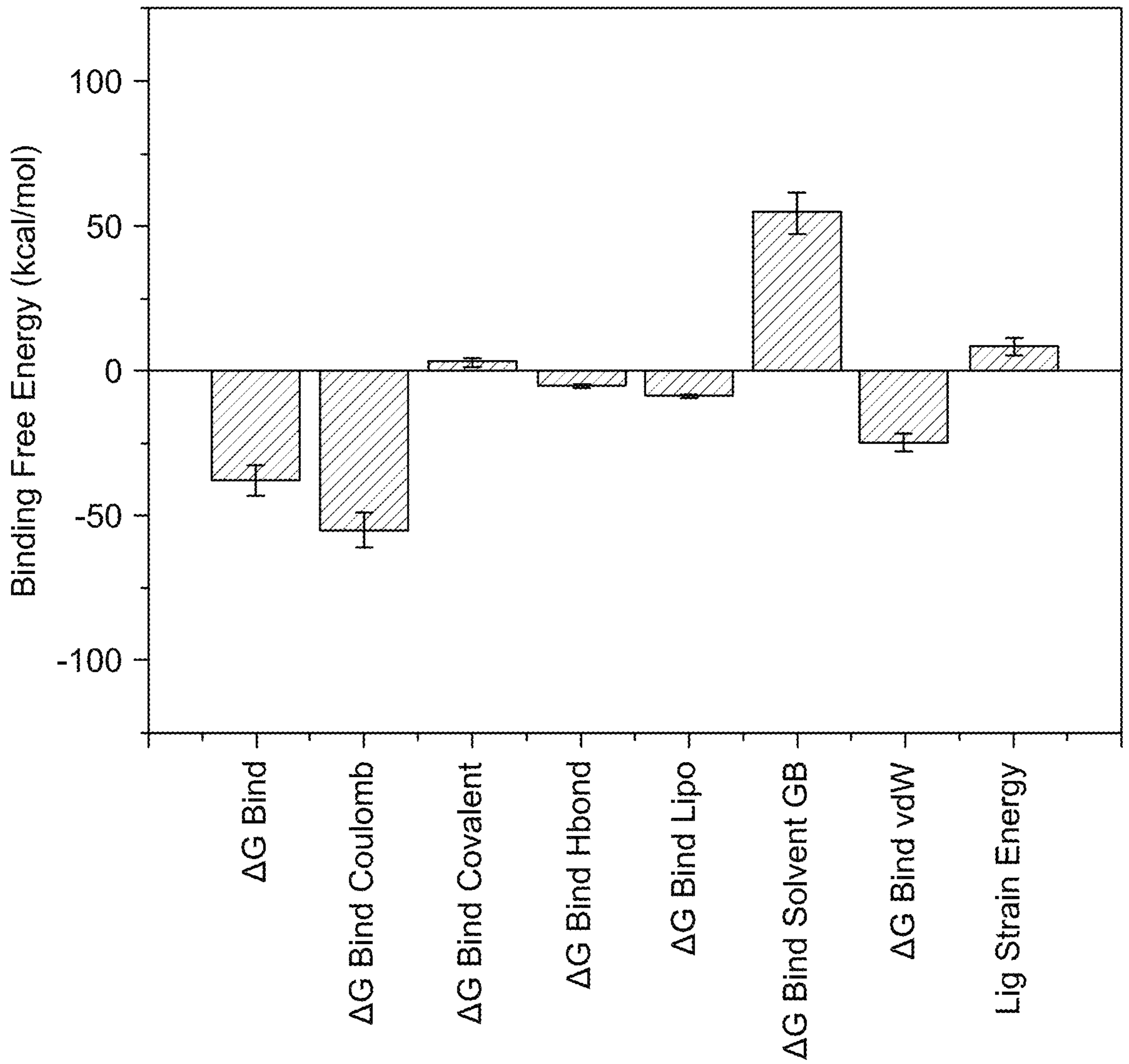
FIG. 7C. Binding free energy analysis of the docked phytochemical compound viz rutin.
Figure 7D:
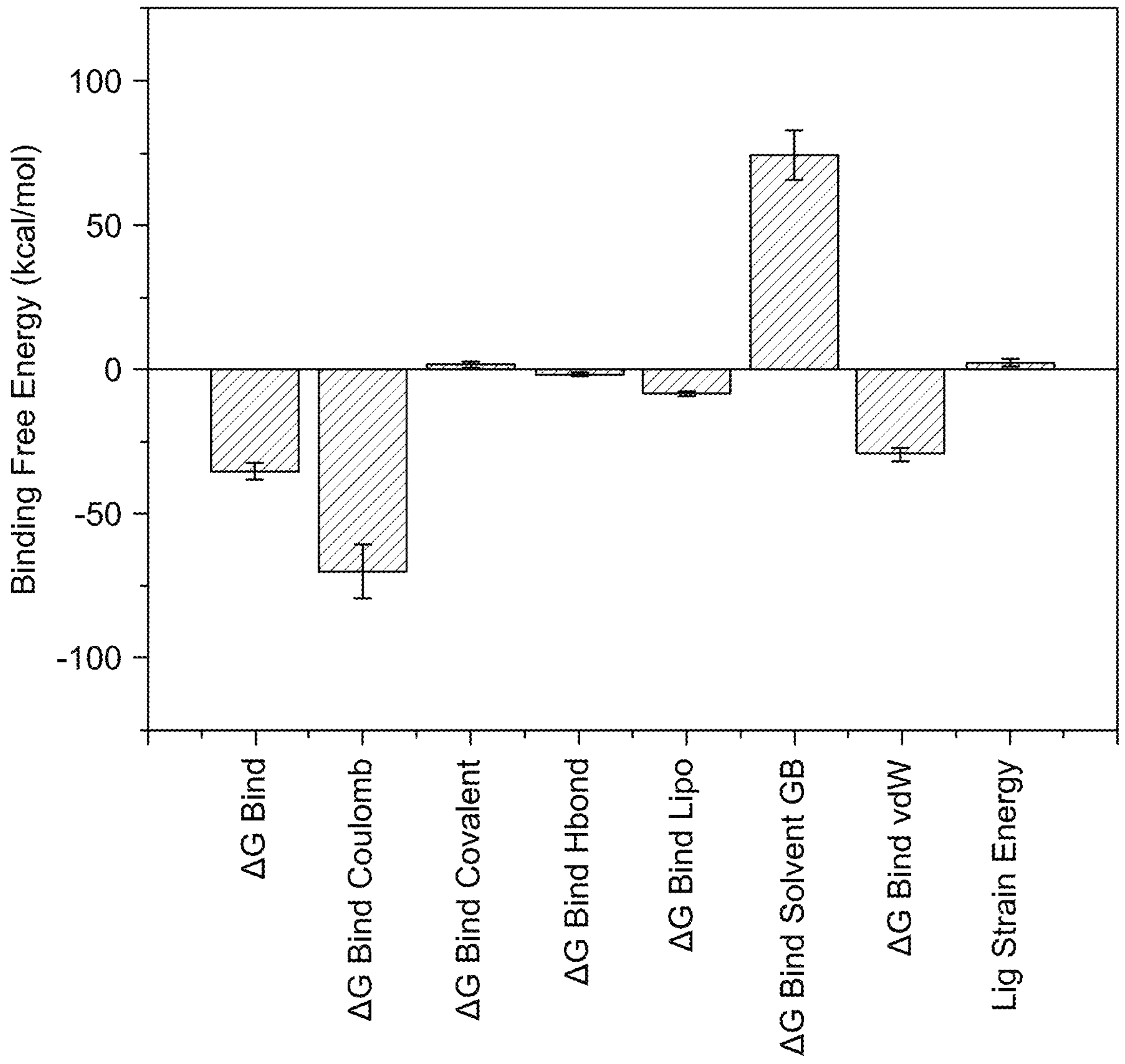
FIG. 7D. Binding free energy analysis of the docked phytochemical compound viz protopseudohypericin.
Figure 7E:
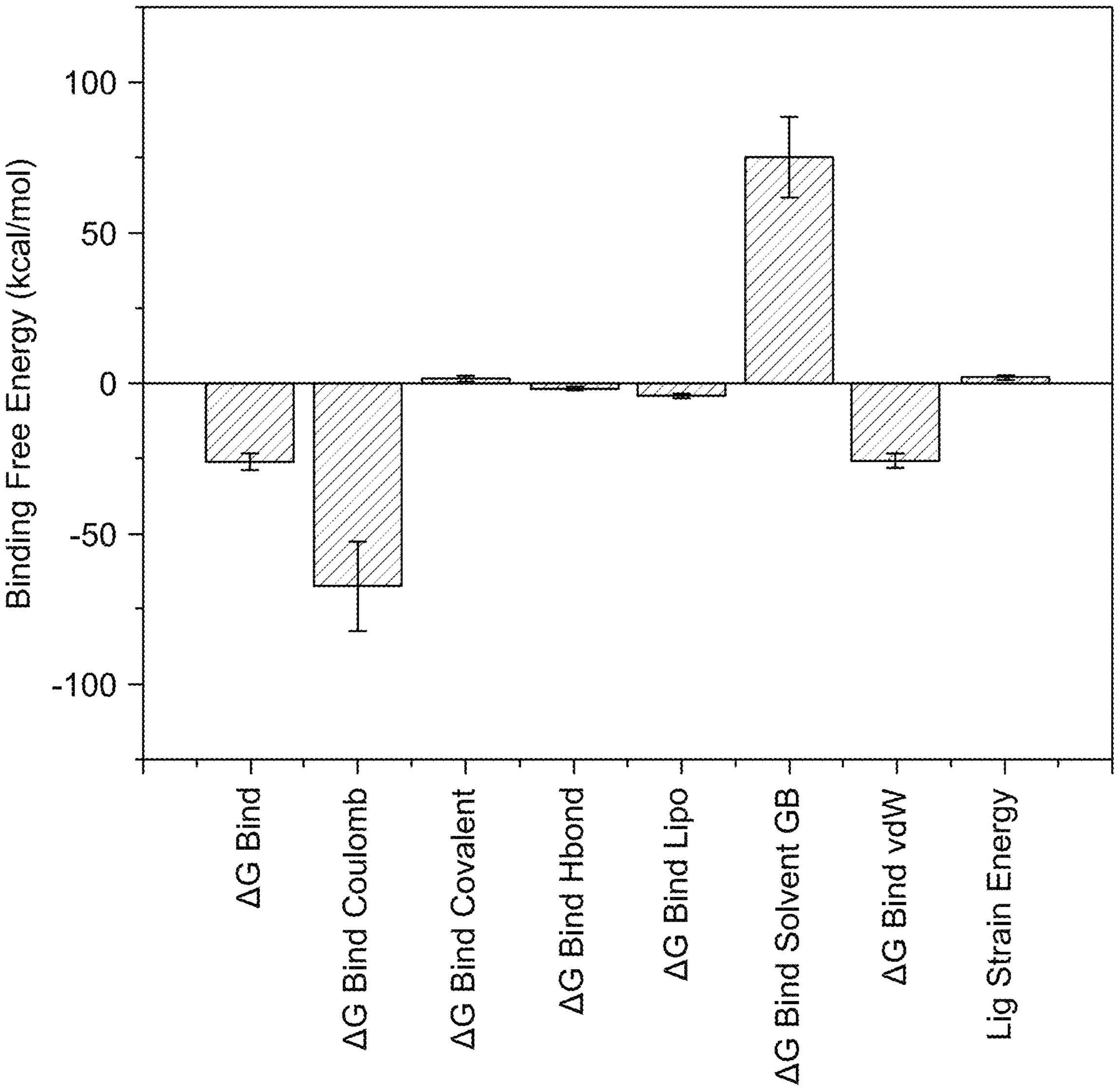
FIG. 7E. Binding free energy analysis of the docked phytochemical compound viz myricetin.
Figure 8A:
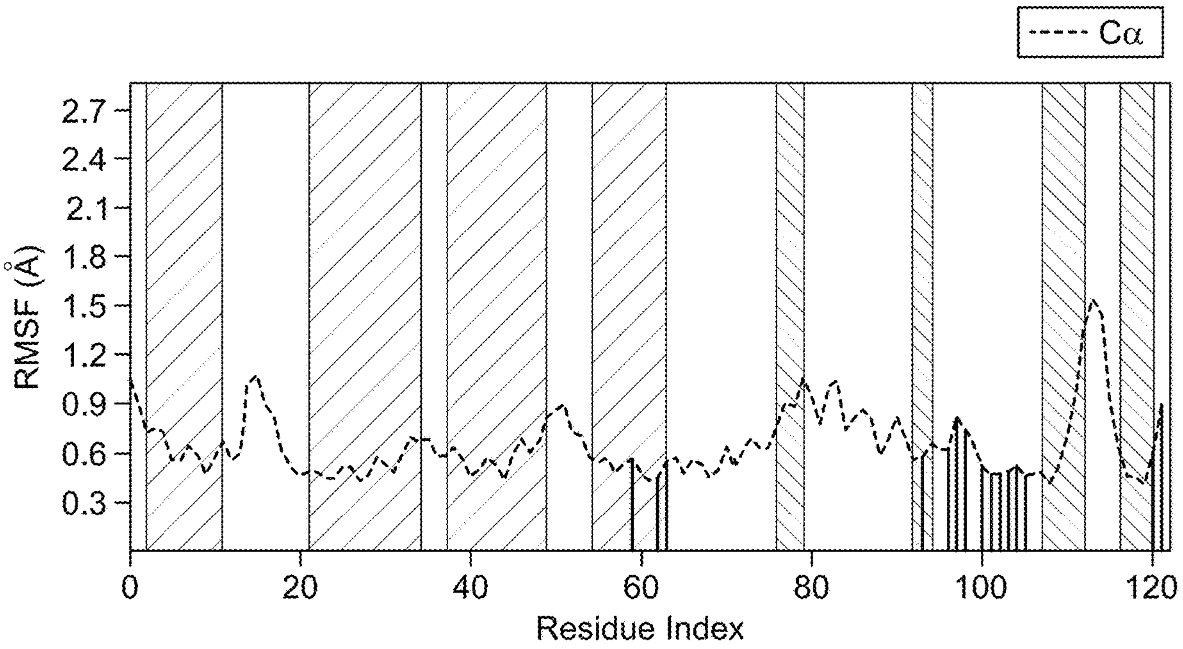
FIG. 8A. Residue index viz kudzuisoflavone A.
Figure 8B:
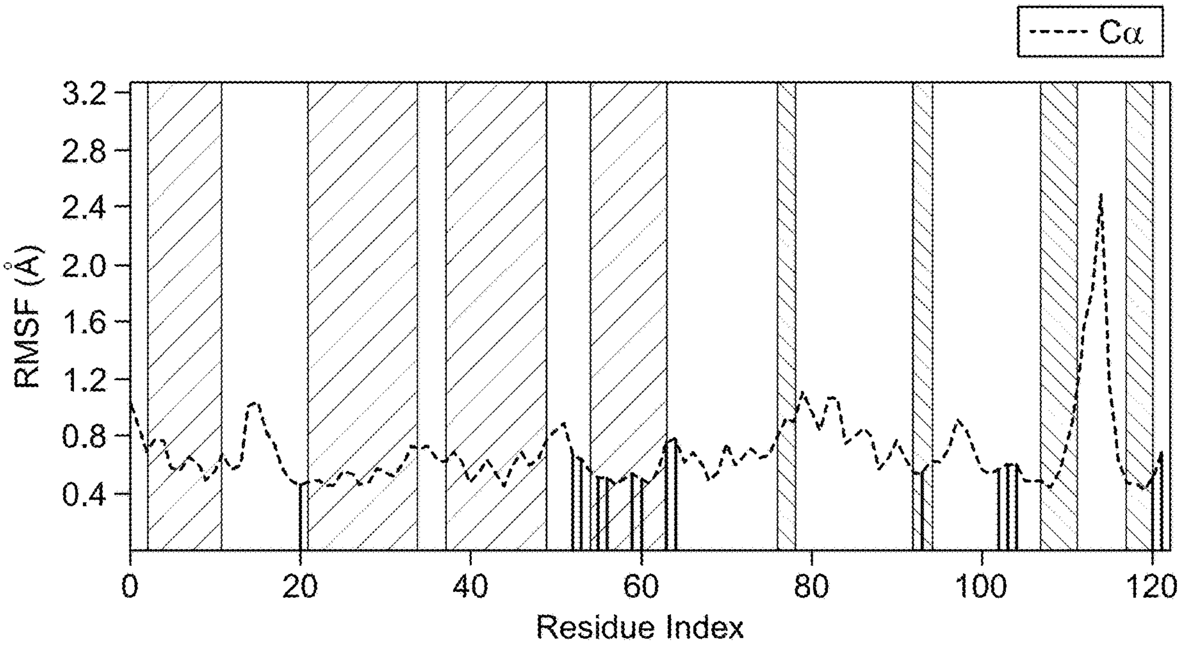
FIG. 8B. Residue index viz miquelianin.
Figure 8C:
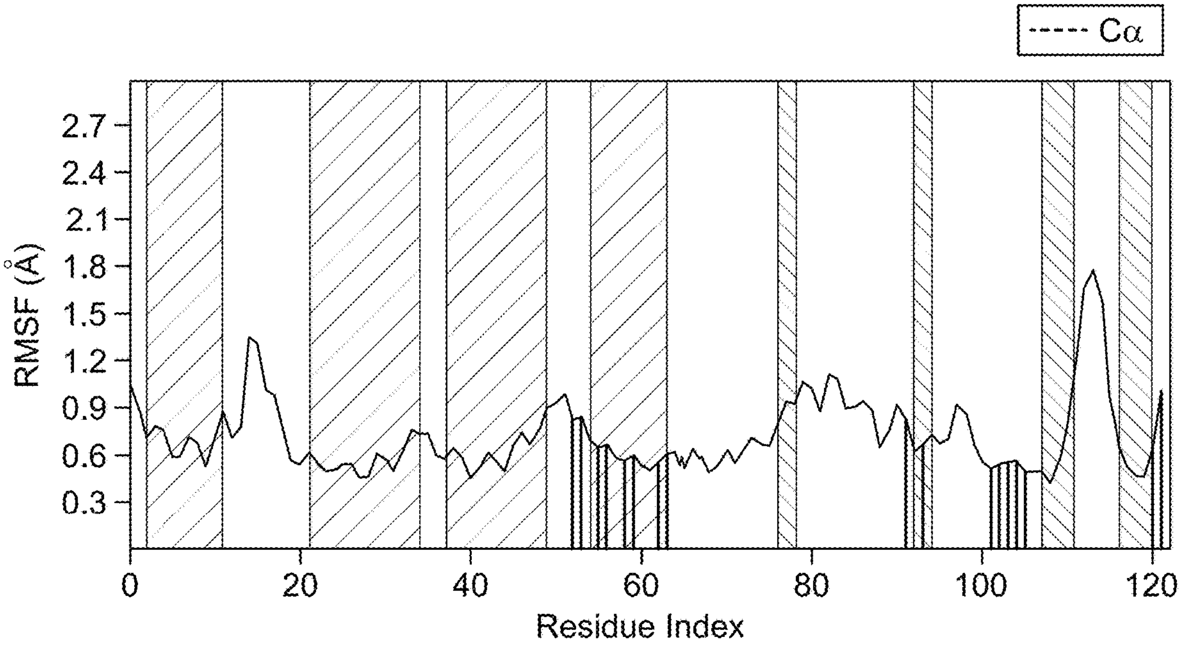
FIG. 8C. Residue index viz rutin.
Figure 8D:
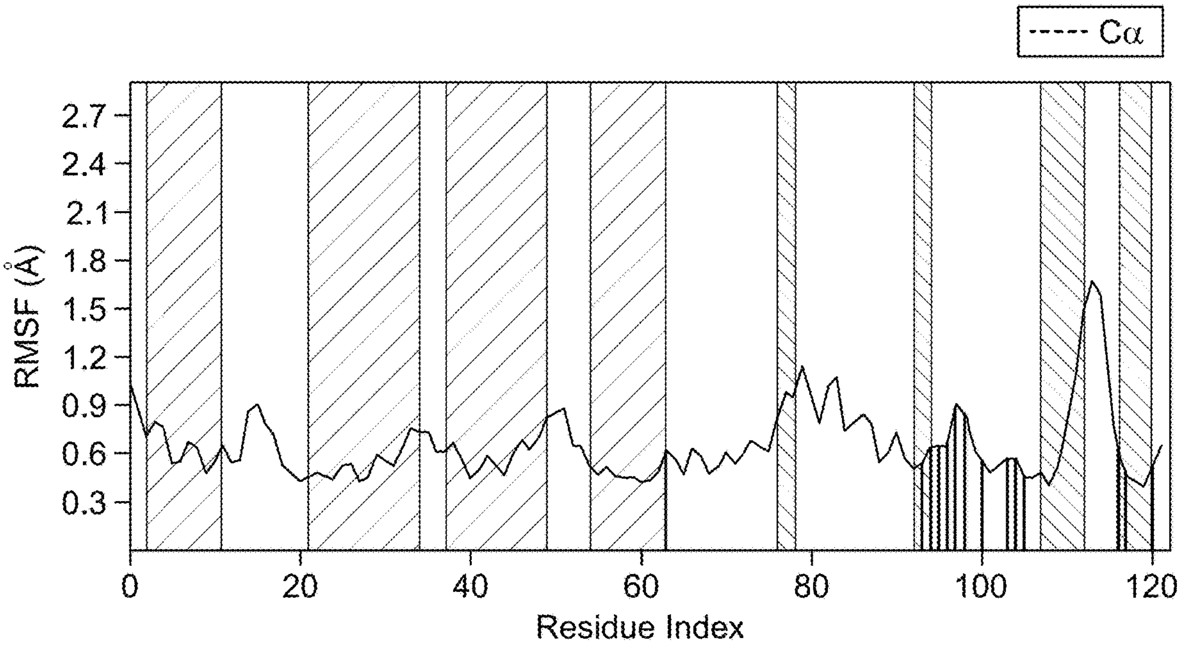
FIG. 8D. Residue index viz protopseudohypericin.
Figure 8E:
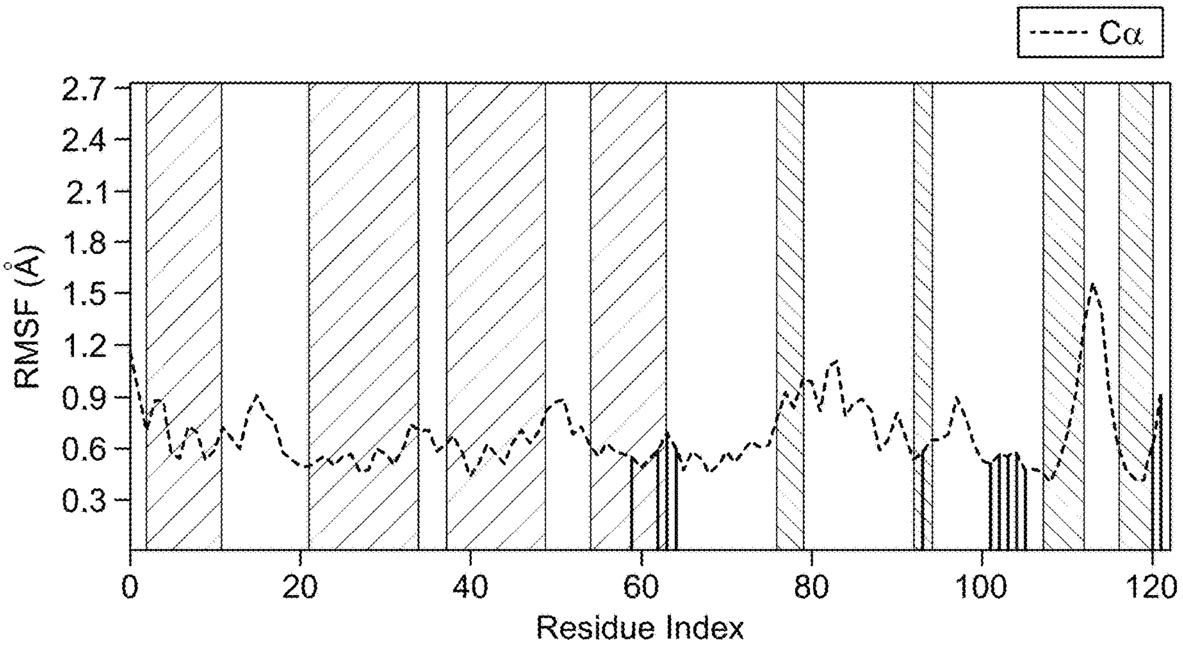
FIG. 8E. Residue index viz myricetin.
Figure 9A:
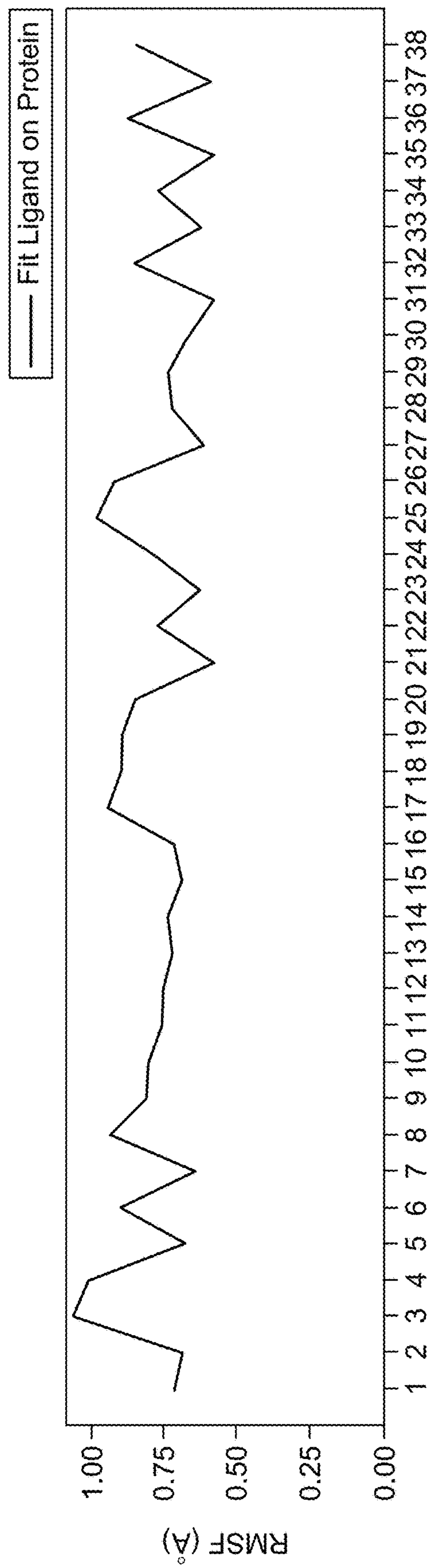
FIG. 9A. Fit ligand on protein viz kudzuisoflavone A.
Figure 9B:
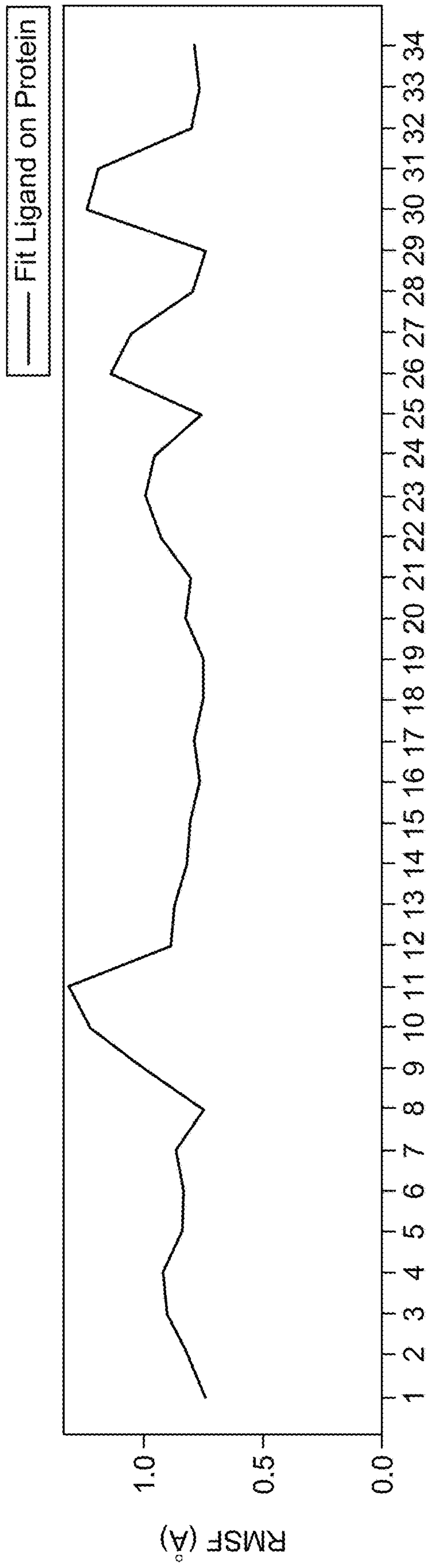
FIG. 9B. Fit ligand on protein viz miquelianin.
Figure 9C:
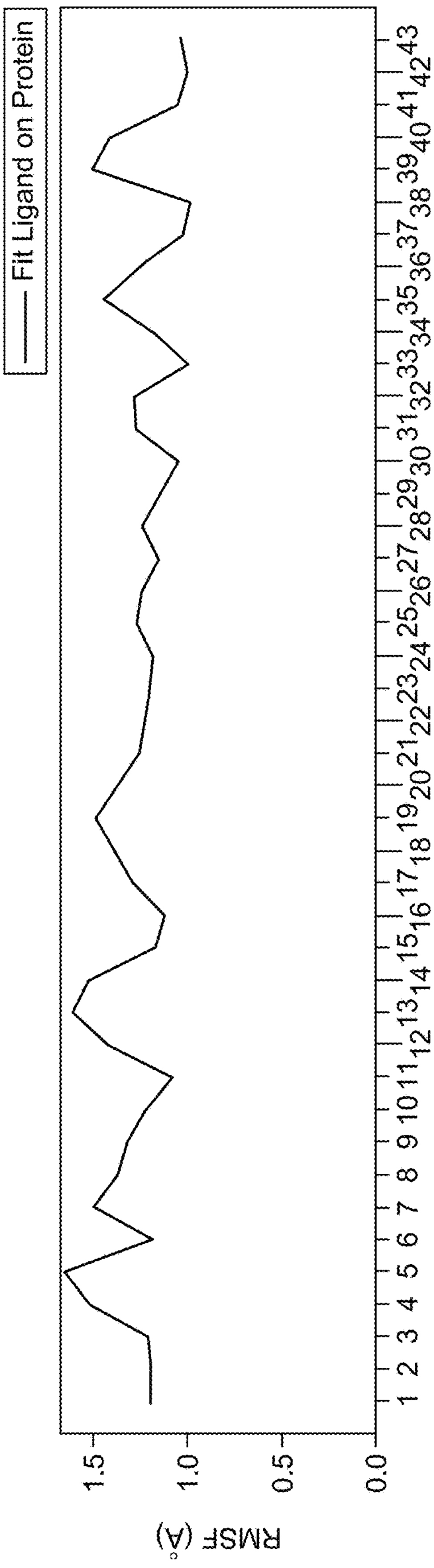
FIG. 9C. Fit ligand on protein viz rutin.
Figure 9D:
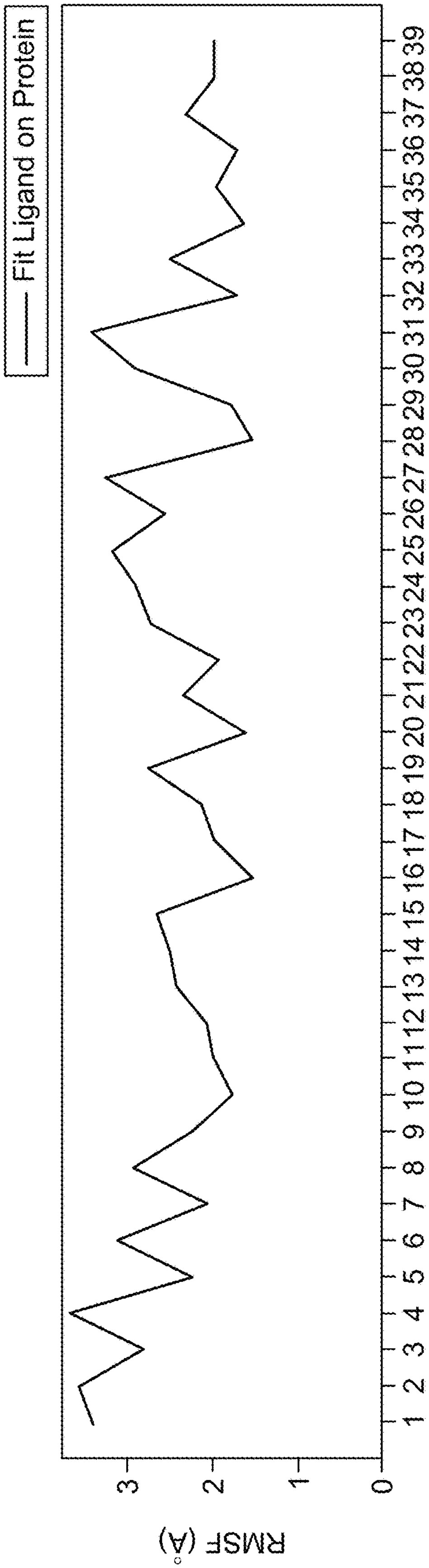
FIG. 9D. Fit ligand on protein viz protopseudohypericin.
Figure 9E:
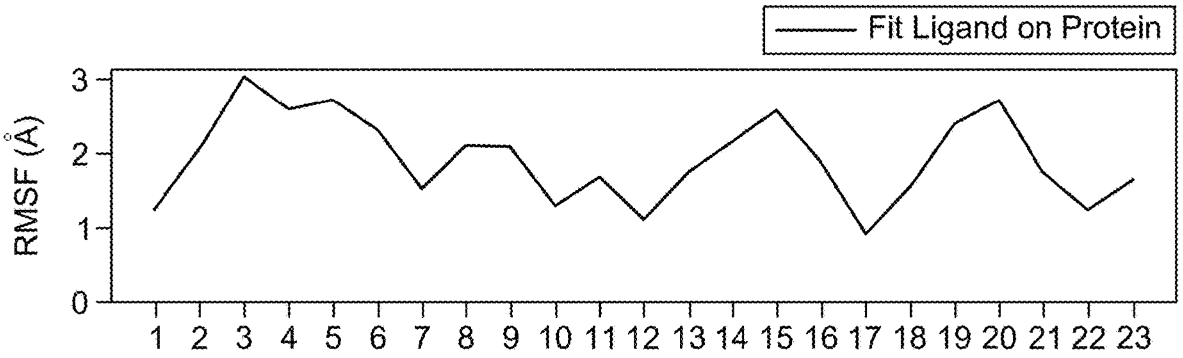
FIG. 9E. Fit ligand on protein viz myricetin.
Figure 10A:
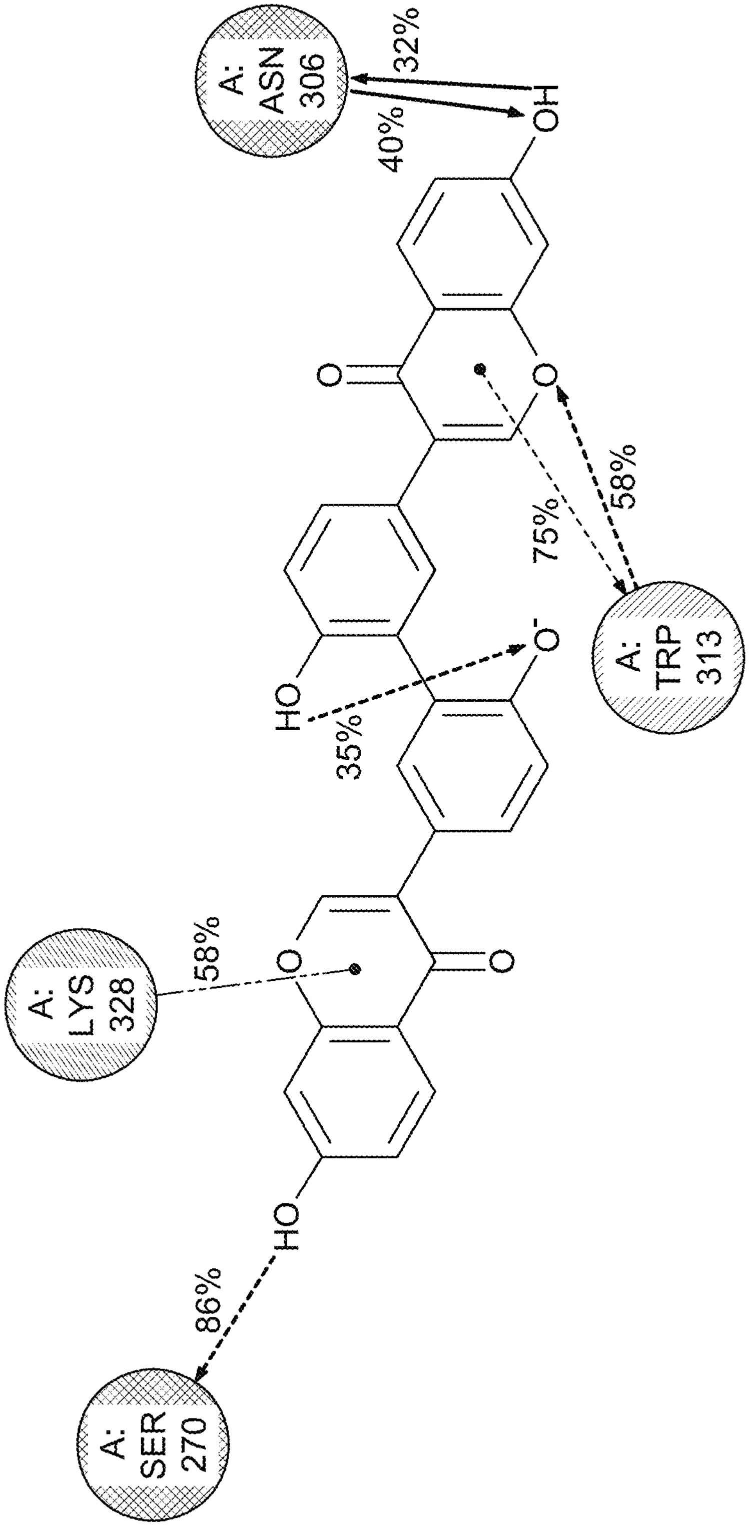
FIG. 10A. Schematic representation of protein-ligand interactions monitored throughout the MD simulation with kudzuisoflavone A.
Figure 10B:
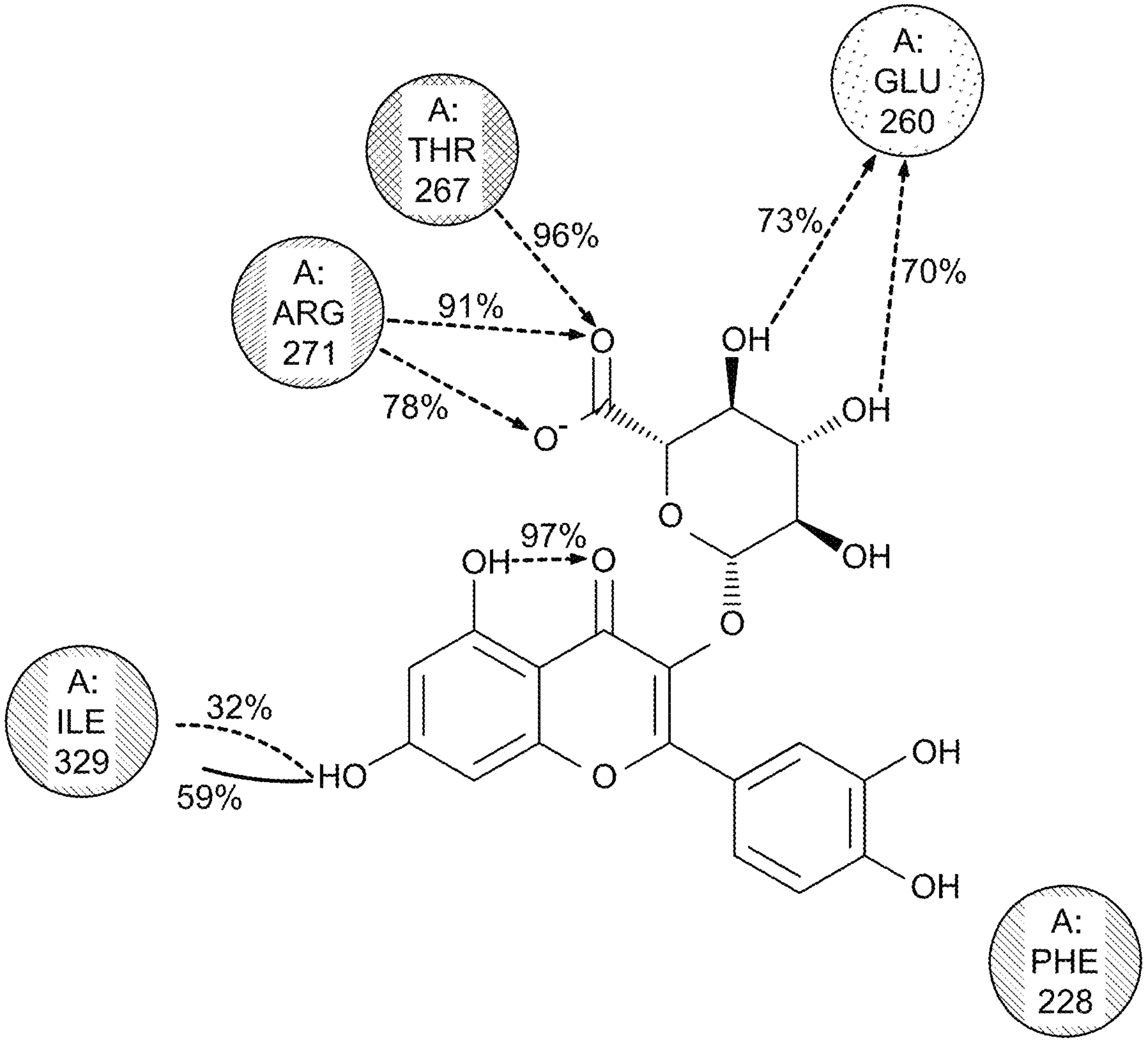
FIG. 10B. Schematic representation of protein-ligand interactions monitored throughout the MD simulation with miquelianin.
Figure 10C:
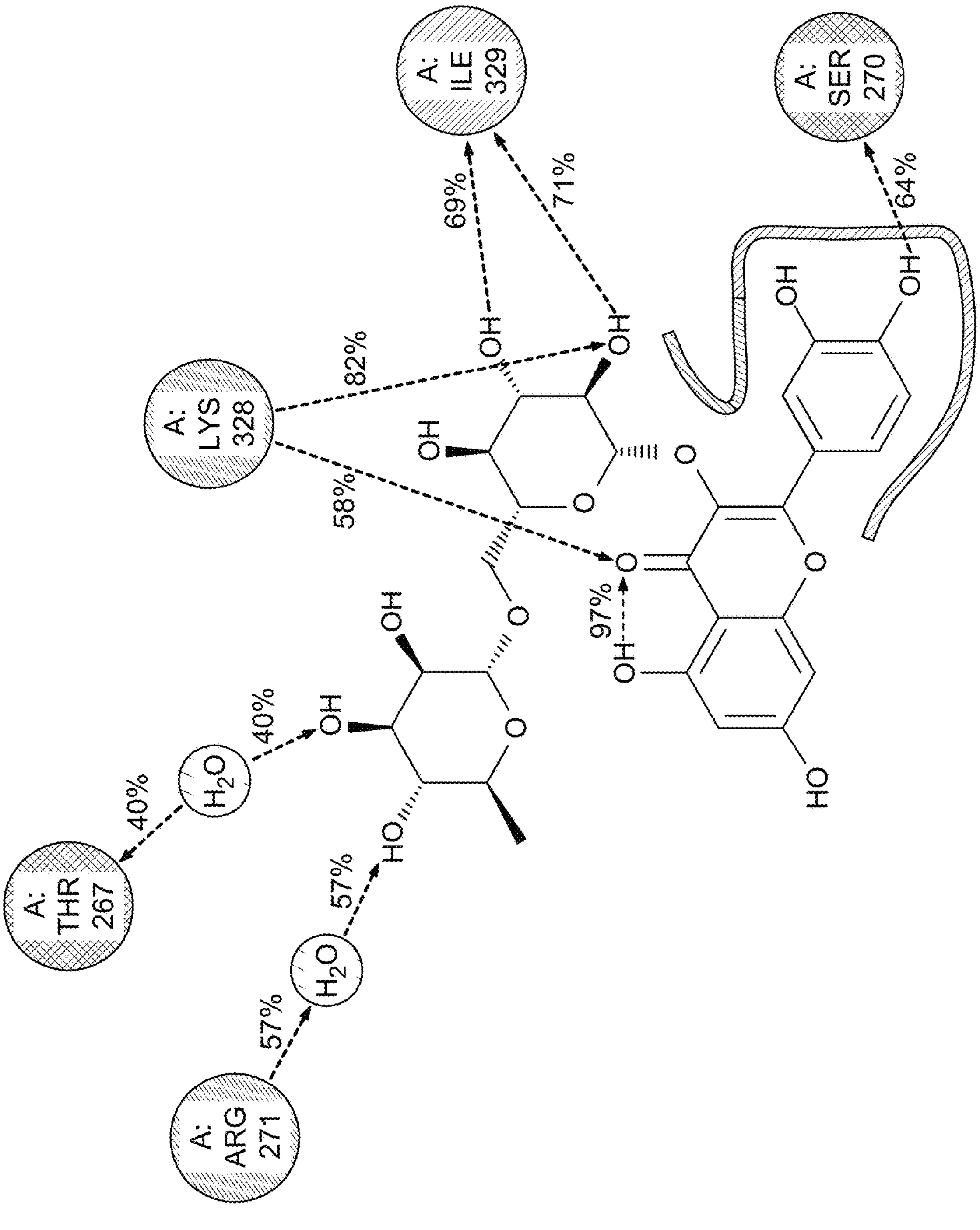
FIG. 10C. Schematic representation of protein-ligand interactions monitored throughout the MD simulation docking with rutin.
Figure 10D:
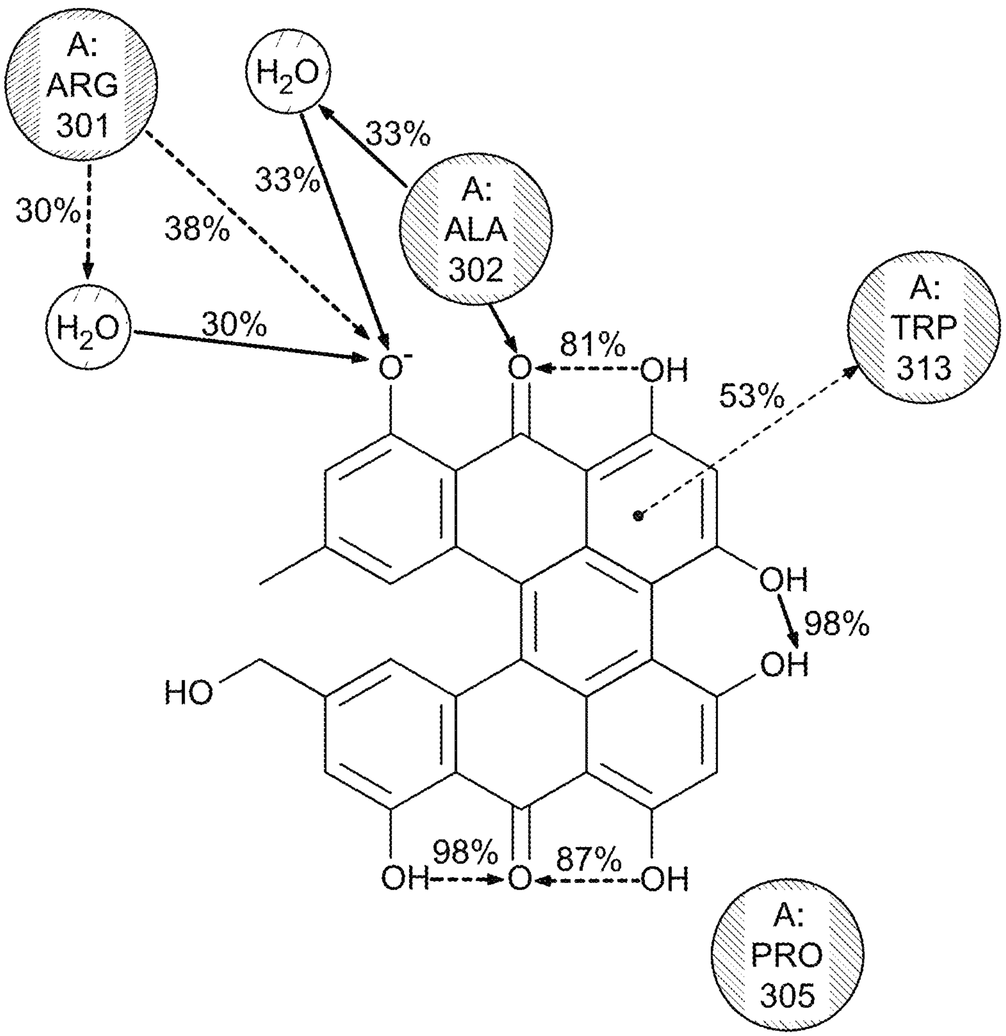
FIG. 10D. Schematic representation of protein-ligand interactions monitored throughout the MD simulation protopseudohypericin.
Figure 10E:
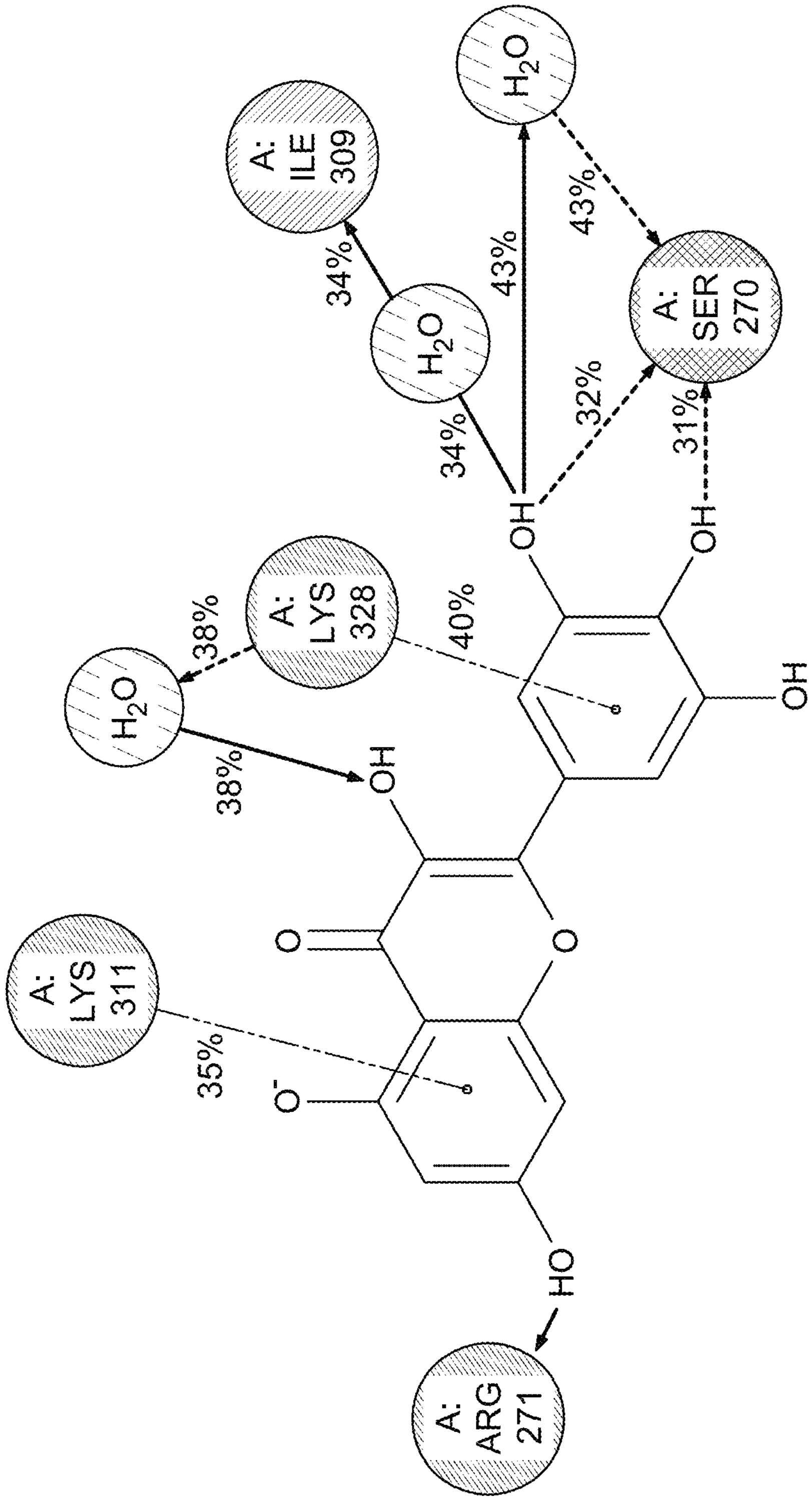
FIG. 10E. Schematic representation of protein-ligand interactions monitored throughout the MD simulation with myricetin.

The free binding energy for reference molecule myricetin (FIGS. 21 and 2J) was −33.57 kcal/mol, suggesting a relatively weaker binding affinity compared to the other compounds. SER-270 and ILE-329 formed hydrogen bonds with reference molecule, while ARG-271 established pi-cation interaction (FIGS. 2I and 2J). These results suggest that the four natural compounds possess the ability to bind to the Marburg virus VP35 protein, potentially affecting its function. The observed binding modes, favorable binding energies, and key interactions between the compounds and the protein residues provide valuable insights into the potential antiviral activity of these natural compounds. FIGS. 2A-2J show the 3D and 2D protein-ligand interaction diagrams of the selected phytochemical compounds kudzuisoflavone A (FIGS. 2A and 2B) miquelianin (FIGS. 2C and 2D), rutin (FIGS. 2E and 2F), Protopseudohypericin (FIGS. 2G and 2H) and the control compound myricetin (FIGS. 21 and 2J).

Example 2

MD Simulation Analysis.

Methodology. The Desmond program was used to run a 100 ns molecular dynamics (MD) simulation to examine the dynamic behavior and interactions of four natural chemicals in association with the Marburg virus VP35 protein [27,28]. Using the three-dimensional structure of the Marburg virus VP35 protein determined from structural information, the protein-ligand complex was first prepared. After that, energy minimization was applied to the protein-ligand combination to minimize any steric interferences or unfavorable interactions. In order to balance the charge in the system, counter ions were introduced after the produced complex was solvated in the appropriate water box. The system was then heated gradually to the required temperature during equilibration, which involved enabling the solvent and the protein-ligand combination to rebalance. The equilibrated system was then simulated using the Desmond program for 100 ns, accurately simulating the interatomic interactions with an appropriate force field (such OPLS3e); see Shivakumar, D.; Williams, J.; Wu, Y.; Damm, W.; Shelley, J.; Sherman, W. Prediction of Absolute Solvation Free Energies Using Molecular Dynamics Free Energy Perturbation and the OPLS Force Field. Journal of chemical theory and computation 2010, 6, 1509-1519—incorporated herein by reference in its entirety.

The protein-ligand complex was given the opportunity to investigate its conformational space and interactions throughout the MD simulation by computationally integrating the equations of motion to propagate the system in time.

The Nosé-Hoover thermostat and the Martyna-Tobias-Klein barostat, respectively, were used to maintain the temperature and pressure throughout the simulation.

The resulting simulation trajectories were examined to assess a number of parameters, such as the root mean square deviation (RMSD) to gauge the stability of the protein-ligand complex, the root mean square fluctuations (RMSF) to examine the flexibility of the protein residues, and the protein-ligand contacts to pinpoint significant interactions.

These investigations contributed to our knowledge of the natural compounds' potential as inhibitors and helped in the development of new therapeutic medicines by offering insightful information about the dynamic behavior, stability, and interactions of the natural compounds with the Marburg virus VP35 protein.

Results. Molecular Dynamics Simulation Analysis. MD simulation mainly focus on the prediction of movement of atoms present in a system during a given time period. To understand this phenomena, each selected protein complex was studied to understand their docking stability till the end of 100 ns simulation. During the analysis of the MD simulation of the protein-ligand complex, the RMSD of each complex is analyzed and these RMSD analysis provides significant information regarding the flexibility of the protein-ligand complex. Also, MD simulation analysis helps to find about the conformational changes, if any, of both protein and ligand until the end of 100 ns simulation.

FIGS. 3A-3E show the 3D structure formation of the initial and the final docked poses of the selected natural compound and the reference complex during the MD simulation. An objective of the first and last post-analysis of the complex was to analyse the structural conformational changes in the protein and ligand molecule of the complexes during the beginning and by the end of the MD simulation. The binding energy of the complexes during the initial phase is mentioned in the virtual screening section and free binding energy analysis of the last ten poses of each complex retrieved from the trajectory was also calculated. These two calculations significantly indicate the ligand's strong binding to the protein molecule Based on the observation of these structures, it was concluded that the final poses undergo certain transitional and rotational variation when compared with the initial pose in all complexes including the reference complex.

FIGS. 3A-3E show the first and last pose analysis of the docked phytochemical compounds kudzuisoflavone A, miquelianin, rutin, protopseudohypericin and myricetin (reference compound) extracted from the simulation trajectories.

RMSD and RMSF Analysis. The molecular dynamics (MD) simulation was performed to investigate the dynamic behavior and structural characteristics of four natural compounds in the complex with the Marburg virus VP35 protein. The simulation provided insights into the stability and interactions of the protein-ligand complexes, as well as the conformational changes of the system. The root mean square deviation (RMSD) analysis was conducted to assess the stability of the protein-ligand complexes during the 100 ns simulation. Kudzuisoflavone A displayed a low RMSD (<2.7 Å), indicating a relatively stable binding throughout the simulation. Miquelianin also exhibited a low RMSD (<2.4) except slightly higher RMSD between a range of 45 to 55 ns time (<3.6 Å) but remained within an acceptable range, suggesting a stable binding. Rutin was showing a higher deviation (<4.5 Å) from starting to 30 ns time after that it was showing stable binding (RMSD<2.5 Å) till 100 ns. Protopseudohypericin demonstrated higher RMSD values (≤10.5 Å) till 23 ns time after that it was stable below ≤4.5 Å RMSD range, indicating more significant conformational changes and flexibility in their binding to the VP35 protein. Myricetin, the reference molecule showed a very low RMSD value (<2.4 Å) till 50 ns simulation time but after 50 ns a higher deviation (≤5.6 Å) was observed. RMSD results analysis indicated that the first two compounds (kudzuisoflavone A and miquelianin) were more stable when compared to the reference molecule; see FIGS. 4A-4E show RMSD plots of the docked phytochemical compound viz kudzuisoflavone A, miquelianin, rutin, protopseudohypericin and myricetin.

To assess the ligand root-mean-square fluctuation (RMSF) as a measure of their flexibility and stability. Kudzuisoflavone displayed a relatively low ligand RMSF of 1.0 Å, indicating a tightly constrained ligand conformation. The miquelianin exhibited an RMSF value of <1.5 Å, suggesting a slightly increased flexibility compared to the first complex. Rutin had an RMSF of 1.5 Å, indicating a similar level of flexibility as the second complex. In contrast, protopseudohypericin demonstrated a significantly higher RMSF value exceeding 3 Å, indicating pronounced ligand fluctuations and potential structural instability. Interestingly, the reference complex exhibited an RMSF value of 3 Å, which aligns with protopseudohypericin, suggesting a comparable level of ligand flexibility and potential dynamic behaviour. These findings highlight the distinct ligand dynamics within the target protein binding pocket. Protopseudohypericin and the reference molecule showed the highest RMSF values, suggesting potentially greater conformational flexibility in these systems; see FIGS. 8A-8E and FIGS. 9A-9E. The smaller value of the residue index & fit ligand (RMSF of protein and ligand) indicates better stability of the protein and ligand in the complex due to their minimum amount of fluctuation.

Protein-ligand interactions monitored throughout the MD simulation. The protein-ligand contacts analysis from MD simulation trajectories and its comparison with the docking pose provided insights into the specific interactions between the compounds and the VP35 protein. The results of the MD simulations revealed that kudzuisoflavone A exhibited stable binding throughout the simulation, maintaining its initial binding pose with the VP35 protein. The compound formed hydrogen bonds with residues SER-270, ASN-306, and TRP-313, and these interactions remained intact during the simulation, contributing to the overall stability of the complex. Miquelianin displayed strong stability during the simulation in its binding pose. It formed hydrogen bonds with residues GLU-260, ASN-261, GLN-263, ARG-271, and ILE-329, although these interactions were strong except for ASN-261 and GLN-263 which were transient and occasionally disrupted. Rutin demonstrated stable binding behavior, with no significant conformational changes and fluctuations in its binding pose. It formed hydrogen bonds with residues THR-267, SER-270, ARG-271, LYS-328, and ILE-329 strongly and stable during simulation except for THR-267 and ARG-271 which were changed into water bridge contacts suggesting a stable binding compared to the reference compound. Protopseudohypericin exhibited relatively weak binding to the VP35 protein, with small fluctuations. The hydrogen bonds with residues ARG-301 and LYS-311 were transient and not sustained throughout the simulation; see FIGS. 10A-10E. The Schematic representation of Protein-ligand interactions monitored throughout the MD simulation represents the interactions that occur more than 30% of the simulation time in the selected trajectory. So, the higher interaction percentage represents better stability.

In comparison while Andrographidine C exhibited strong absorption, distinguishing, metabolism and excretion (ADME) qualities for target V40, Bisandrographolid exhibited several shortcomings including low water solubility and lack of drug likeness score requirements. Its weak pharmacokinetic qualities make it less effective for in vivo use.

FIGS. 5A-5E show protein-ligand interaction monitored throughout the MD simulation of kudzuisoflavone A, miquelianin, rutin, and protopseudohypericin and reference compound myricetin. Overall, the molecular dynamics simulation results provide valuable insights into the structural characteristics and dynamic behavior of the kudzuisoflavone A, miquelianin, rutin, and protopseudohypericin in a complex with the Marburg virus VP35 protein. Kudzuisoflavone A and miquelianin demonstrated more stable binding modes, with consistent interactions, lower RMSD, and less fluctuation in RMSF compared to the reference molecule. the maximum number of bonds for a longer simulation time emphasizes the stable nature of the complex. The stacked bar charts are normalized over the course of the trajectory: for example, a value of 0.7 suggests that 70% of the simulation time the specific interaction is maintained. Values over 1.0 are possible as some protein residue may make multiple contacts of the same subtype with the ligand.

Principal component analysis (PCA) of 100 ns MD simulation trajectories of the Marburg virus VP35 protein in complex with identified natural compounds a revealed that the first three principal components (PC1, PC2 and PC3) accounted for a significant portion of the total variance in the data. The scatter plot generated from the PCA results demonstrated distinct clustering patterns, indicating different conformational dynamics induced by the phytochemical compounds. Each compound exhibited a unique region in the scatter plot, suggesting specific effects on the protein dynamics. The loading plot provided insights into the residues that contributed most to the observed conformational changes. Based on the cluster analysis of each docked complex it was observed that, all the conformers represent by the dots are overlapped, which indicates that the protein-ligand complex shows similar poses in every second of the simulation trajectories and contributes in protein stability. Also the curve slope formation in the scree plot also suggests that these complex supports these findings. So, according to the PCA analysis all the selected complexes have minimum number of dissimilar conformers and remain in stable state compared and the reference complex VP35. Myricetin (control ligand) shows a certain variance in the conformation of the protein dynamics. FIGS. 6A-6E provide PCA analysis of the docked phytochemical compound viz kudzuisoflavone A, miquelianin, rutin, and protopseudohypericin and reference compound myricetin.

Example 3

Free Binding Energy Calculation

The Prime module of the Schrodinger Suite was used to perform the MM-GBSA analysis of molecular dynamics simulation trajectories (from 91 to 100 ns) of four natural chemicals in combination with the Marburg virus VP35 protein. The process involved taking the protein-ligand complexes from the simulated trajectories and applying the OPLS3e force field to optimize the structures [29]. The molecular mechanics-generalized Born surface area (MM-GBSA) approach, which combines surface area calculations, generalized Born solvation energy calculations, and molecular mechanics energy calculations to estimate the changes in binding free energies, was used to calculate the binding free energies.

Results: Binding free energy analysis. The MM/GBSA method was used to calculate the net free binding of extracted poses of each docked complex from the last 10 ns of the extended MD simulation trajectory. Moreover, each compound's energy dissociation components were also calculated to study their involvement in the overall stability of the identified phytochemical with viral protein. The free binding energy analysis for the selected compounds docked with VP35 protein, showed that complex VP35-Kudzuisoflavone A displayed maximum free binding energy (ΔGBind=−47.16+1.15) compared to all other selected phytochemical docked complex. Also the free binding energy of this complex was also higher than the reference complex VP35-Myricetin (ΔGBind=−26.27+2.51). Based on these observations in was concluded that VP35 when docked with Kudzuisoflavone A compound exhibits maximum stability compared to the reference compound. Also, the stability analysis of the complexes based on the energy dissociation components, also signifies that ΔGBind Coulomb and ΔGBind vdW majorly contribute to complex stability, whereas ΔGBind Solv GB contributes in the destabilization of the complexes including the reference complex, FIGS. 7A-7E show binding free energy analysis of the docked phytochemical compound viz a) kudzuisoflavone A, b) miquelianin, c) rutin, and d) protopseudohypericin and reference compound myricetin. In the binding free energy analysis, the relative binding free energy value (ΔGBind) property best emphasizes this feature of the work.

Example 4

Principal Component Analysis (PCA) The trajectories of four natural chemicals in a combination with the Marburg virus VP35 protein were subjected to a principal component analysis (PCA) using molecular dynamics (MD) simulations. The Desmond program's MD simulation trajectory data was first transformed using the VMD software into DCD file format. The initial conformation of the protein-ligand complexes was also captured by extracting the first pose of each MD simulation trajectory.

After that, the PCA analysis was carried out in R using the Bio3D package; see Grant, B. J.; Rodrigues, A. P.; ElSawy, K. M.; McCammon, J. A.; Caves, L. S. Bio3d: An R Package for the Comparative Analysis of Protein Structures. Bioinformatics 2006, 22, 2695-2696—incorporated herein by reference in its entirety. In order to acquire the principal components for the PCA analysis, the eigenvalue decomposition step was followed by computing the covariance matrix of the atomic fluctuations in the retrieved poses and simulation trajectories. With the help of this research, the dynamics and interactions of the protein-ligand complexes' collective movements and conformational changes were better understood.

Results: PCA of 100 ns MD simulation trajectories of the Marburg virus VP35 protein in complex with identified natural compounds a revealed that the first three principal components (PC1, PC2 and PC3) accounted for a significant portion of the total variance in the data. The scatter plot generated from the PCA results demonstrated distinct clustering patterns, indicating different conformational dynamics induced by the phytochemical compounds. Each compound exhibited a unique region in the scatter plot, implicating specific effects on the protein dynamics. The loading plot provided insights into the residues that contributed most to the observed conformational changes. Based on the cluster analysis of each docked complex it was observed that, all the conformers represent by the dots are overlapped, which indicates that the protein-ligand complex shows similar poses in every second of the simulation trajectories and contributes in protein stability. Also the curve slope formation in the scree plot also implicates that these complex supports these findings. So, according to the PCA analysis all the selected complexes have minimum number of dissimilar conformers and remain in stable state compared and the reference complex VP35—Myricetin (control ligand) show certain variance in the conformation of the protein dynamics. FIGS. 6A-6E show PCA analysis of the docked phytochemical compound viz kudzuisoflavone A, miquelianin, rutin, and protopseudohypericin and reference compound myricetin.

As disclosed herein the advantages of using in silico drug discovery techniques to locate effective inhibitors that specifically target the RNA binding activity of the Marburg virus VP35 protein has been demonstrated. Four inhibitors from the medicinal herbs Adiantum capillus-veneris, *Hypericum* perforatum, and *Pueraria montana* (kudzuisoflavone A, miquelianin, rutin, and protopseudohypericin) were successfully identified during the experiment. Molecular dynamics simulation analysis of all the selected molecules revealed that kudzuisoflavone A and miquelianin exhibited stable binding and favorable interactions with the Marburg virus's VP35 protein, surpassing the free binding energies of the reference molecule myricetin. The VP35 protein kept its structural stability after binding to the inhibitor, according to principal component analysis. These results offer insightful information about the molecular interactions and binding dynamics of the inhibitors' binding to the Marburg virus's VP35 protein. This work demonstrates the antiviral activities of these medicinal plants as important sources of active antiviral compounds specifically target the Marburg virus via VP33.

Terminology used herein is for the purpose of describing particular embodiments only and is not intended to be limiting of the invention.

Unless expressly stated, the terms used herein are intended to have the plain and ordinary meaning as understood by those of ordinary skill in the art.

The following definitions are intended to aid the reader in understanding the present disclosure but are not intended to vary or otherwise limit the meaning of such terms unless specifically indicated.

While aspects of the present disclosure have been described in conjunction with the specific embodiments thereof that are proposed as examples, alternatives, modifications, and variations to the examples may be made. The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the technology.

It should be noted that, as used in the specification and the appended claims, the singular forms "a," "an," and "the" include plural referents unless the context clearly dictates otherwise.

As used herein, the term "and/or" includes any and all combinations of one or more of the associated listed items and may be abbreviated as "/". A and/or B includes A, B, and (A+B).

As used herein in the specification including as used in the examples and unless otherwise expressly specified, all numbers in the specification may be read as if prefaced by the word "substantially", "about" or "approximately," even if the term does not expressly appear. Numbers in the claims refer to their exact values unless otherwise specified.

The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−0.2% of the stated value (or range of values), +/−0.5% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges and values subsumed therein.

Any numerical range recited herein is intended to include all sub-ranges and values subsumed therein. Where a range of values is provided, it is to be understood that each intervening value between an upper and lower limit of the range and any other stated or intervening value in that stated range is encompassed within the disclosure. Where the stated range includes upper and lower limits, ranges excluding either of those limits are also included.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-2, 1-3, 1-4, 1-5, 1-6, 1-7, 1-8, 1-9, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10, 9-10 as some examples. A range encompasses its endpoints as well as values inside of an endpoint, for example, the range 0-5 includes 0, >0, 1, 2, 3, 4, <5 and 5.

As referred to herein, all compositional percentages are by weight of the total composition, unless otherwise specified.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references and does not constitute an admission as to the accuracy of the content of such references.

The invention claimed is:

1. A method for treating a subject exposed to or infected by Marburg virus, comprising administering to the subject at least one component selected from the group consisting of kudzuisoflavone A, miquelianin, or protopseudohypericin in an amount sufficient to bind to, antagonize, or inhibit activity of Marburg virus VP35 protein.

2. The method of claim 1, wherein the subject has been exposed to Marburg virus but is asymptomatic.

3. The method of claim 1, wherein the subject has been infected by Marburg virus.

4. The method of claim 1, wherein the at least one component is administered in an amount that inhibits the replication of Marburg virus.

5. The method of claim 1, wherein the at least one component is administered in an amount that reduces VP35 antagonism of interferon, reduces inhibition of interferon regulatory factor 3, reduces VP35-inhibition of protein kinase R activation, or otherwise inhibits the ability of the Marburg virus to evade host immune responses.

6. The method of claim 1, wherein the at least one component is administered in an amount that inhibits dimerization or oligomerization VP35.

7. A method for treating a subject exposed to or infected by Marburg virus, comprising administering to the subject kudzuisoflavone A in an amount sufficient to bind to, antagonize, or inhibit activity of Marburg virus VP35 protein.

8. A method for treating a subject exposed to or infected by Marburg virus, comprising administering to the subject miquelianin or protopseudohypericin in an amount sufficient to bind to, antagonize, or inhibit activity of Marburg virus VP35 protein.

9. The method of claim 8, wherein the at least one component comprises miquelianin.

10. The method of claim 8, wherein the at least one component comprises protopseudohypericin.

11. The method of claim 1, wherein the at least one component is administered orally, sublingually, buccally, topically, or by another non-enteric route.

12. The method of claim 1, wherein the at least one component is administered intraperitoneally, intravenously, intramuscularly, or by another parenteral route.

13. The method of claim 1, further comprising administering tilorone, quinacrine, pyronaridine, favipiravir, GS-5734, or other antiviral drug to the subject.

14. The method of claim 1, further comprising replacing lost blood and clotting factors, administering supplemental oxygen, and/or administering water and electrolytes to the subject.

* * * * *